US012485236B2

(12) United States Patent
Li et al.

(10) Patent No.: US 12,485,236 B2
(45) Date of Patent: Dec. 2, 2025

(54) ELECTRONIC ATOMIZATION DEVICE AND ATOMIZATION ASSEMBLY

(71) Applicant: Shenzhen Smoore Technology Limited, Shenzhen (CN)

(72) Inventors: Guanghui Li, Shenzhen (CN); Weidong Pan, Shenzhen (CN); Kui Li, Shenzhen (CN); Zhenyu Wu, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 37 days.

(21) Appl. No.: 18/733,368

(22) Filed: Jun. 4, 2024

(65) Prior Publication Data

US 2024/0316295 A1 Sep. 26, 2024

Related U.S. Application Data

(63) Continuation of application No. 17/903,066, filed on Sep. 6, 2022, now Pat. No. 12,042,601, which is a (Continued)

(30) Foreign Application Priority Data

Sep. 5, 2018 (CN) ......................... 201811033876.0
Nov. 29, 2018 (CN) ......................... 201811447699.0

(51) Int. Cl.
*A24F 40/10* (2020.01)
*A24F 40/40* (2020.01)

(Continued)

(52) U.S. Cl.
CPC ............. *A61M 15/06* (2013.01); *A24F 40/10* (2020.01); *A24F 40/40* (2020.01); *A61M 15/002* (2014.02)

(58) Field of Classification Search
CPC ........... A24F 40/44; A24F 40/40; A24F 40/10
See application file for complete search history.

(56) References Cited

U.S. PATENT DOCUMENTS

2012/0199663 A1* 8/2012 Qiu ......................... A24F 40/42
239/8
2017/0360092 A1* 12/2017 Althorpe ............... A61M 15/06

(Continued)

FOREIGN PATENT DOCUMENTS

CN 204317503 U 5/2015
CN 106418728 A 2/2017

(Continued)

*Primary Examiner* — Alex B Efta

(57) ABSTRACT

The present disclosure may provide an atomizer and an electronic atomization device. The atomizer may include a shell, a heating assembly, a lid, a base, and a first sealing component. The shell defines a liquid cavity and a smoke outlet. The heating assembly may heat and atomize the liquid into a smoke. The lid and the base may be provided to fix the heating assembly therebetween. The lid defines a liquid inlet communicating with the liquid cavity, and the liquid may flow through to reach the heating assembly. The atomizer may define an air entering hole, such that external air may enter the device through the hole to drive smoke to flow. The first sealing component may be engaged between the lid and the heating assembly, contacting both at the same time and defining air guiding channels to guide the air to flow into the liquid cavity.

20 Claims, 13 Drawing Sheets

Related U.S. Application Data continuation of application No. 16/691,555, filed on Nov. 21, 2019, now Pat. No. 11,471,625, which is a continuation of application No. PCT/CN2019/104577, filed on Sep. 5, 2019.

(51) Int. Cl.

| | |
|---|---|
| ***A61M 15/00*** | (2006.01) |
| ***A61M 15/06*** | (2006.01) |

(56) References Cited

U.S. PATENT DOCUMENTS

| | | | | |
|---|---|---|---|---|
| 2019/0014822 | A1 * | 1/2019 | Bless ................ | A61M 15/0036 |
| 2020/0022417 | A1 | 1/2020 | Atkins | |
| 2020/0128874 | A1 | 4/2020 | Atkins | |

FOREIGN PATENT DOCUMENTS

| | | | | | |
|---|---|---|---|---|---|
| CN | 207202044 | U | 4/2018 | | |
| CN | 108185536 | A | 6/2018 | | |
| WO | 2017028295 | | 2/2017 | | |
| WO | WO-2017028295 | A1 * | 2/2017 | ............. | A24F 40/44 |

* cited by examiner

II-II

II-II

ELECTRONIC ATOMIZATION DEVICE AND ATOMIZATION ASSEMBLY

CROSS REFERENCE TO RELATED APPLICATIONS

The present application is a continuation-application of U.S. patent application Ser. No. 17/903,066, filed Sep. 6, 2022, which is a continuation-application of U.S. patent application Ser. No. 16/691,555, filed Nov. 21, 2019, now U.S. Pat. No. 11,471,625, which is a continuation-application of International (PCT) Patent Application No. PCT/CN2019/104577 filed on Sep. 5, 2019, which claims foreign priorities of Chinese Patent Application No. 201811033876.0, filed on Sep. 5, 2018, and Chinese Patent Application No. 201811447699.0, filed on Nov. 29, 2018, in the National Intellectual Property Administration of China, the entire contents of which are hereby incorporated by reference in their entireties.

TECHNICAL FIELD

The present disclosure relates to the field of electronic atomization device, and in particular to an electronic atomization device and an atomization assembly.

BACKGROUND

An electronic atomization device is also called a virtual cigarette or an electronic atomizer. It may be used to replace an actual cigarette. The electronic atomization device may generate similar taste as the actual cigarette does, but may not contain tar, and other harmful components.

An electronic atomization device in the related art may include an atomizer and a battery assembly. While the atomizer is atomizing aerosol-generating substrate, consumption of the aerosol-generating substrate may facilitate generation of negative pressure, which may result in obstructed flow of the liquid, generating a burnt flavor, bringing unfavoured user experience.

SUMMARY OF THE DISCLOSURE

According to an aspect of the present disclosure, an electronic atomization device is provided. The electronic atomization device includes: a tube wall, a heating assembly, and a sealing component. The tube wall defines a liquid cavity for storing liquid to be vaporized. The heating assembly is arranged to heat and atomize the liquid flowing from the liquid cavity to generate a smoke. The sealing component is arranged between the tube wall and the heating assembly for sealing, and air guiding channels are defined between the sealing component and at least one of the tube wall and the heating assembly. The air guiding channels communicate with the liquid cavity.

According to another aspect of the present disclosure, an atomization assembly adapted for an electronic atomization device is provided. The atomization assembly includes: a tube wall, a liquid guiding member, a seal, and a heating component. The tube wall defines at least a liquid cavity and a smoke outlet. The liquid guiding member includes a top wall and a sidewall, a recess recessing from the top wall toward a bottom of the liquid guiding member. The seal encloses the top wall and an upper portion of the sidewall. The seal includes a top engaging portion enclosing the top wall and a side engaging portion enclosing the upper portion of the sidewall. The seal has an uneven inner face such that air guiding channels are defined between the seal and the liquid guiding member. The seal further has an outer face to abut against the tube wall. The heating component is provided on the bottom of the liquid guiding member and configured to heat the liquid guiding member.

DETAILED DESCRIPTION

The present disclosure is to be further described clearly and comprehensively by referring to appended figures and embodiments. Described embodiments herein are only a part of, but not all of, the possible embodiments. Based on the described embodiments of the present disclosure, ordinary skilled in the art may obtain other embodiments without contributing creative endeavor, which should be within the scope of the present disclosure.

Figure 1:
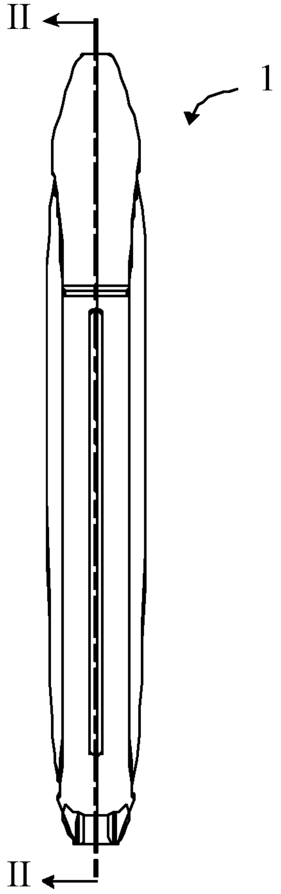
FIG. 1 is a side view of an electronic atomization device according to an embodiment of the present disclosure.
Figure 2:
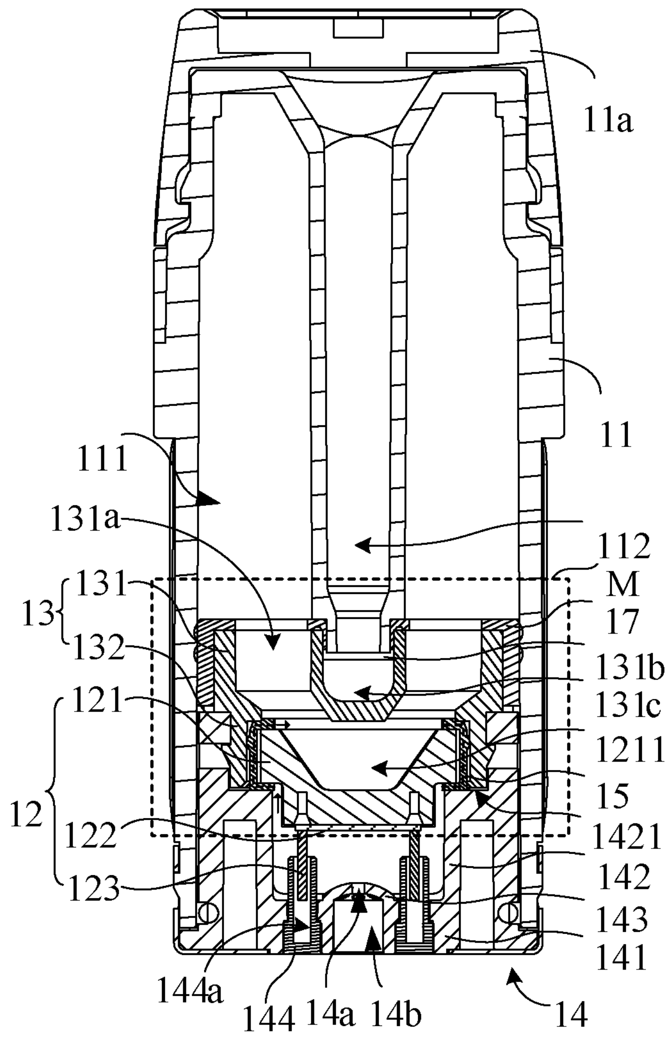
FIG. 2 is a cross section view of the atomizer at a position II-II according to embodiment shown in FIG. 1.
Figure 3:
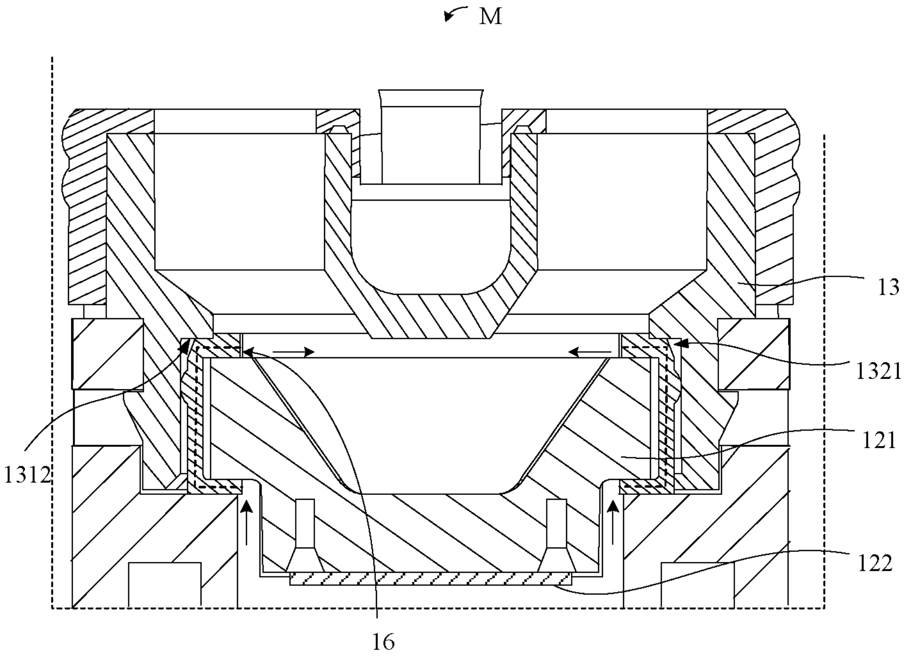
FIG. 3 is an enlarged view of a portion M of the atomizer according to the embodiment shown in FIG. 2.

Referring to FIG. 1, an electronic atomization device 1 may be provided, some components of the electronic atomization device may be heated by electric current to steam aerosol-generating substrate to generate a smoke, and the some components may be a device for atomization. The aerosol-generating substrate can be heated and vaporized to generate aerosol or smoke. In this embodiment, the aerosol-generating substrate may be a liquid. The components of the electronic atomization device 1 for atomizing the liquid may be an atomizer as shown in FIG. 2. Referring to FIG. 2 and FIG. 3, an atomizer of an embodiment of the present disclosure may include: a shell 11, a heating assembly 12, a lid 13, a base 14, and a first member 15.

The shell 11 may define a liquid cavity 111 to store a liquid, and a smoke outlet 112. The heating assembly 12 may be arranged to heat the liquid stored in the liquid cavity 111 and atomize the liquid to generate a smoke. For example, when the liquid in the liquid cavity 111 flows to reach the heating assembly 12, the liquid may be heated and atomized to generate the smoke. The generated smoke may flow through the smoke outlet 112 to reach a user to be inhaled.

In the present embodiment, the heating assembly 12 may be engaged between the lid 13 and the base 14, wherein the lid 13 and the base 14 may be fixed with respect to each other, such that the heating assembly 12 may be fixedly arranged between the lid 13 and the base 14. The lid 13 may define a liquid inlet 131*a*, and the liquid inlet 131*a* may communicate with the liquid cavity 111. The liquid in the liquid cavity 111 may flow through the liquid inlet 131*a* to reach the heating assembly 12. The atomizer may further define an air entering hole 14*a* to allow external air to enter the atomizer. For example, the base 14 may define the air entering hole 14*a*, communicating with an external, such that the external air may enter the atomizer through the air entering hole 14*a*, driving the smoke to flow into the smoke outlet 112.

In the present embodiment, the first sealing member 15 may be arranged between the lid 13 and the heating assembly 12, contacting the lid 13 and the heating assembly 12 at the same time for sealing. In such a way, when the liquid flows from the liquid cavity 111 through the liquid inlet 131*a* to the heating assembly 12, the liquid may not be leaked from a position at which the lid 13 contacts or connects with the heating assembly 12. In other words, the first sealing member 15 may seal the connected or contact position between the lid 13 and the heating assembly 12. Further referring to FIG. 3, an air guiding channel 16 may be defined between the first sealing member 15 and the heating assembly 12. The air guiding channel 16 may at least guide the external air entering from the air entering hole 14*a* to the liquid cavity 111. To be specific, the external air may enter the base 14 through the air entering hole 14*a*, and flow into the air guiding channel 16, further flowing through the liquid inlet 131*a* entering the liquid cavity 111.

According to the present embodiment, the liquid in the liquid cavity 111 may flow through the liquid inlet 131*a* of the lid 13 to reach the heating assembly 12. The heating assembly 12 may heat and atomize the liquid to generate the smoke. With a pressure generated by a user while inhaling, air may enter the atomizer from the base 14 through the air entering hole 14*a*. The pressure may create air flow, driving the smoke to flow into the smoke outlet 112, and the smoke may be inhaled by the user.

In the related art, as the liquid may continuously flow to the heating assembly 12 for atomization, a pressure in the liquid cavity 111 may be reduced to become a negative pressure. Therefore, flowing of the liquid to the heating assembly 12 for atomization may be blocked, resulting in an obstructed downward flow of the liquid. Also, the liquid which is already on the heating assembly 12 may not be able to flow, such that a burnt taste may be generated, impacting user experience. In order to solve the technical problem, the present disclosure may provide a first sealing member 15 between the lid 13 and the heating assembly 12, and an air guiding channel 16 may be defined between the first sealing member 15 and the heating assembly 12. The air guiding channel 16 may at least guide the air entering from the air entering hole 14*a* to the liquid cavity 111 to increase the pressure inside the liquid cavity 111, such that the liquid in the liquid cavity 111 may not be blocked from flowing downward, increasing efficiency of the atomizer and improving user experience.

In the present embodiment, the shell 11 may be provided to define a hollow tube, of which the shape may be designed according to actual demands of the electronic atomization device, such as a cylinder or elliptic cylinder shape. The smoke outlet 112 may also be defined as tubular, extending along a length direction of the shell 11. An end of the smoke outlet 112 may communicate with a smoke vent defined by a mouthpiece 11*a*, and the other end of the smoke outlet 112 receiving the smoke generated by the heating assembly 12. The liquid cavity 111 may be defined between an outer side wall of the smoke outlet 112 and an inner side wall of the shell 11, and may store the liquid. Further, the shell 11 may define a pouring hole (not shown in the figure) for liquid to be added, wherein the pouring hole may communicate with the liquid cavity 111. The pouring hole may be sealed while not in use. Alternatively, along a direction starting from the mouthpiece 11*a* to the heating assembly 12, a width of the shell 11 may increase gradually at the beginning and then maintain when reaching a certain width. In other embodiments, the air entering hole 14*a* may be defined on the mouthpiece 11*a* and further communicate with the smoke outlet 112. In such a way, when the user inhales, pressure may be generated, allowing external air to enter the smoke outlet 112 through the air entering hole 14*a*, forming an air flow to drive the smoke to flow.

Figure 4:
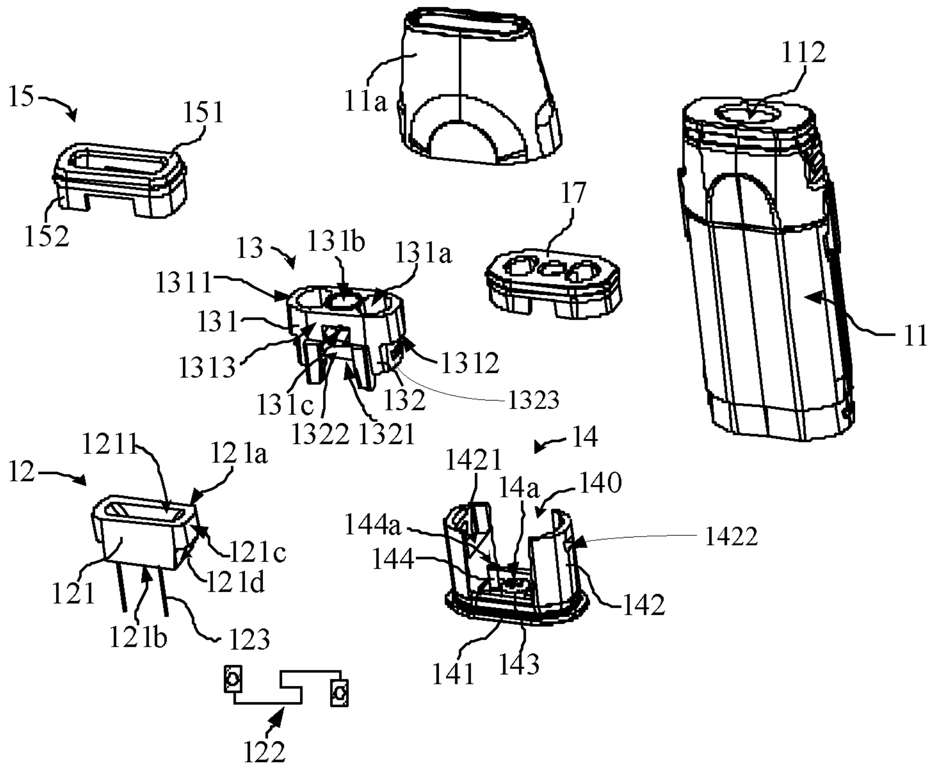
FIG. 4 is an exploded perspective view of an atomizer according an embodiment of the present disclosure.

Referring to FIG. 2 and FIG. 4, alternatively, the heating assembly 12 may include a porous ceramic liquid guiding member 121 and a heating member 122, mounted on a bottom face 121*b* of the porous ceramic liquid guiding member 121. The porous ceramic liquid guiding member 121 may be made of a ceramic material having a plurality of pores, wherein the ceramic may contain aggregates, binders, and pore-forming agents, and undergo a sintering process. A plurality of pores may be defined within the ceramic, communicating with each other and with surfaces of the ceramic. The ceramic may have high porosity, be chemically stable, and have a large specific surface area, a small volumetric density, a low thermal conductivity, corrosion and thermal resistance. In the present embodiment, defining the air guiding channel 16 further allows ventilation of the smoke while flowing through a bending-structured porous liquid guiding member 121, such that the burnt taste due to the obstructed downward flow of the liquid may be reduced, increasing efficiency of the atomizer and improving user experience.

To be specific, the porous ceramic liquid guiding member 121 may define a liquid guiding groove 1211. For example, the porous ceramic liquid guiding member 121 may have a top face 121*a* facing the liquid cavity 111, and the top face 121*a* may be embedded inwards to define the liquid guiding groove 1211. The liquid flowing through the liquid inlet 131*a* may be received in the liquid guiding groove 1211. The liquid guiding groove 1211 may have a plurality of cross surfaces parallel with the top face 121*a* of the porous ceramic liquid guiding member 121, an area of each of the plurality of cross surfaces may decrease gradually along a depth direction starting from the bottom face 121*b* towards the top face 121*a* of the porous ceramic liquid guiding member 121. By defining the liquid guiding groove 1211, the liquid may be easily received, and a contact area between the liquid and the porous ceramic liquid guiding member 121 may be improved, thus, increasing flowing efficiency and a flowing speed of the liquid.

In the present embodiment, the heating member 122 may comprise at least one of the following: a heating coating, a heating circuitry, a heating plate or a heating net. To be specific, the heating member 122 may be provided on the bottom face 121*b* of the porous ceramic liquid guiding member 121, wherein the bottom face 121*b* is opposite to the liquid guiding groove 1211. The liquid may flow through the porous structure of the ceramic liquid guiding member 121, reaching the heating member 122 at the bottom face 121*b*, wherein the heating member 122 may be connected to a power to heat and atomize the liquid, generating the smoke. In the present embodiment, the heating member 122 may be a heating resistance wire. After the heating member 122 is connected to the power to be heated, the liquid flowing through the porous ceramic liquid guiding member 121 reaching the bottom face 121*b* may be atomized to generate the smoke. In the present embodiment, the heating member 122 may be twisted and turned.

Referring to FIG. 2 and FIG. 4, the heating assembly 12 may further include an electrode 123, an end of the electrode 123 may be inserted into the bottom face 121*b* of the porous ceramic liquid guiding member 121, and the other end of the electrodes 123 may extend away from the bottom face 121*b*. That is, when the heating assembly is fixed between the lid 13 and the base 14, an end of the electrode 123 may be inserted into the bottom face 121*b*, and the other end of the electrode 123 may extend towards the base 14. The electrode 123 may be electrically connected to the heating member 122 and the power. Two electrodes 123 may be provided, one of the two electrodes may be connected to a positive pole, and the other one of the two electrodes may be connected to a negative pole of the power. The power may be a battery.

Referring to FIG. 2 and FIG. 4, the lid 13 may include a guiding portion 131 and a housing portion 132, connected with each other. The guiding portion 131 may define the liquid inlet 131*a*, and the liquid inlet 131*a* may extend through the guiding portion from a top 1311 to a bottom 1312. In the present embodiment, two of the liquid inlets 131*a* may be defined spaced apart from each other, and each of the two liquid inlets 131*a* may communicate with each of two liquid cavities 111, wherein the two liquid cavities 111 may be defined at two sides of the smoke outlet 112. The liquid inlet 131*a* may communicate with the liquid cavity 111 at the top 1311 of the guiding portion 131, and further communicate with the liquid guiding groove 1211 at the bottom 1312 of the guiding portion 131. The liquid inlet 131*a* may be elliptical, and areas of cross surfaces of the liquid inlet 131*a* may decrease gradually along a direction starting from the top 1311 towards the bottom 1312. In the present disclosure, the lid 13 may be manufactured as an integral component.

Referring to FIG. 2 to FIG. 4, in the present embodiment, a side wall of the housing portion 132 may extend from an outer edge of the bottom 1312 of the guiding portion 131 to define a chamber 1321. Distance between the side wall of the housing portion 132 and periphery of the liquid inlet 131*a* may be greater than 0, wherein the liquid inlet 131*a* may be defined at the bottom 1312 of the guiding portion 131, That is, due to distance between an inner surface (facing the chamber 1321) of the side wall of the housing portion 132 and the periphery of the liquid inlet 131*a* being greater than 0, for example, the distance may be equal to 0.3 mm, a portion of the bottom 1312 may be between the side wall of the housing portion 132 and the periphery of the liquid inlet 131*a*, and may be capable of abutting against the first sealing member 15 for sealing. This is to ensure the sealing effect of the first sealing member 15 and avoiding leakage of the liquid. The chamber 1321 may receive a portion of the heating assembly 12. The first sealing member 15 may be received in the chamber 1321, supporting the guiding portion 131 and the heating assembly 12 for sealing. To be specific, an opening of the chamber 1321 may be opposite to the bottom 1312 of the guiding portion 131. The first sealing member 15 and the porous ceramic liquid guiding member 121 may be received into the chamber 1321 through the opening. The first sealing member 15 may be supported between the bottom 1312 of the guiding portion 131 and the top face 121*a* of the porous ceramic liquid guiding member 121 for sealing, reducing possibility of the liquid being leaked from a gap between the bottom 1312 of the guiding portion 131 and the porous ceramic liquid guiding member 121, such that the liquid may be guided into the liquid guiding groove 1211 directly.

Alternatively, the guiding portion 131 may further define an air outlet 131*b* at the top 1311. In the present embodiment, the air outlet 131*b* may be defined adjacent to the liquid inlet 131*a*, and spaced apart from the liquid inlet 131*a*. The guiding portion 131 may further define a through hole 131*c*, wherein the through hole 131*c* may extend through two opposing side surfaces 1313 of the guiding portion 131. In the present embodiment, one of the side surfaces 1313 of the guiding portion 131 may be a surface non-adjacent to a side wall 142 of the base 14. The through hole 131*c* may communicate with the air outlet 131*b*. That is, the air outlet 131*b* may be defined by the bottom 1312 and an inner surface of the side wall 1313 of the guiding portion 131, such that the smoke may flow through the through hole 131*c* and the air outlet 131*b*, entering the smoke outlet 112. In the present embodiment, the air outlet 131*b* may communicate with the smoke outlet 112. For example, side walls of the smoke outlet 112 may be inserted into the air outlet 131*b* and sealed with the air outlet 131*b*. Further, an outer surface of the side wall of the housing portion 132 may define a guiding groove 1322, and the guiding groove 1322 may communicate with the through hole 131*c* of the guiding portion 131. The guiding groove 1322 may extend from a position at which the guiding groove 1322 communicates with the through hole 131*c* towards an end of the housing portion 132 away from the guiding portion 131. Referring to FIG. 2 and FIG. 4, the atomizer may further include a second sealing member 17, provided to be a case, at least covering edges of the top 1311 and periphery of the guiding portion 131 of the lid 13, such that the shell 11 may be sealed with the lid 13 to avoid leak of the liquid in the liquid cavity 111. Further, when the second sealing member 17 encases the lid 13 for sealing, it may also seal a gap between the side wall of the smoke outlet 112 and the side wall of air outlet 131*b*. In such a way, a possibility of the liquid being leaked from the air outlet may be reduced, and a possibility of smoke leaking may be reduced. In the present embodiment, the second sealing member 17 may be made of silicone as an integral component.

Referring to FIG. 2 and FIG. 4, alternatively, the base 14 may include a bottom wall 141 and a side wall 142 connecting with the bottom wall 141. For example, there may be two side walls 142 arranged oppositely and spaced apart from each other. As shown in FIG. 4, the two side walls 142 may not be arranged to form a closed loop, and define a receiving space 140, which may receive the heating assembly 12. The housing portion 132 may be received in the receiving space 140 and fixed with respect to the two side walls 142, such that the heating assembly 12 may be fixed between the lid 13 and the base 14. When receiving the housing portion 132 into the receiving space 140, the guiding groove 1322 may communicate with the receiving space 140 and the through hole 131*c*, such that the receiving space 140 may communicate with the smoke outlet 112. In the present embodiment, alternatively, the air entering hole 14*a* may be defined on the bottom wall 141, and the air entering hole 14*a* may extend through the bottom wall 141 vertically. The air entering hole 14*a* may also be defined on at least one of the two side walls 142, or defined on at least one of the two side walls 142 and the bottom wall 141. In other embodiments, the air entering hole 14*a* may not be defined on the base 14, as the air entering hole 14*a*, the smoke outlet 112, the air outlet 131*b*, the through hole 131*c*, the guiding groove 1322, and the receiving space 140 may be inter-communicated, the air entering from the air entering hole 14*a* may still flow into the receiving space 140, and continue flow through the air guiding channel 16, entering the liquid cavity 111. In the present embodiment, the two side walls 142 of the base and the housing portion 132 may be buckling connected. For example, a buckle groove 1422 may be defined on the side wall 142 of the base, and a buckle block 1323 may be formed on an outer side wall of the housing portion 132. When the housing portion 132 received into the receiving space 140, the buckle block may be engaged into the buckle groove for fixing. Further, the guiding groove 1322 of the housing portion 132 may communicate with the receiving space 140 and the through hole 132*c*.

Further referring to FIG. 2 and FIG. 4, in the present embodiment, the base 14 may further include an electrode hole mount 144. An end of the electrode hole mount 144 may be protruded from a side of the bottom wall 141 facing the lid 13, and the other end of the electrode hole mount 144 may be exposed at an opposing side of the bottom wall 141 facing away from the lid 13. The end of the electrode hole mount 144 facing away from the lid 13 may be a blind via, functioning as an electrode hole 144*a*. A portion of another end of the electrode hole mount 144 exposed at the opposing side of the bottom wall 141 facing away from the lid 13 may be a contact pin to connect to the power. In the present embodiment, the electrode 123 of the heating assembly 12 may be inserted into the electrode hole 144*a* of the electrode hole mount 144, and the electrode hole mount 144 may be connected to the power to allow the electric current to heat the heating member 122. Further, the liquid in the guiding groove 1211 may flow through the porous structure of the porous ceramic liquid guiding member 121 reaching the heating member 122 located on the bottom face 121*b*, and vaporized to form a smoke by the heated heating member 122. The smoke may be formed in the receiving space 140. Further referring to FIG. 2 and FIG. 4, alternatively, the bottom wall 141 of the base may define an air vent 14*b*, communicating with the external. The base 14 may further include an air inlet board 143, and the air inlet board 143 may define a plurality of air entering holes 14*a*. The plurality of air entering holes 14*a* may communicate with the receiving space 140 of the base 14 and the air vent 14*b*, such that external air may flow through the air vent 14*b* and the air entering holes 14*a*, entering the receiving space 140. The receiving space may be defined between the base 14 and the heating assembly 12. The smoke generated by atomization of the liquid functioned by the heating member 122 arranged at the bottom face 121*b* of the porous ceramic liquid guiding member 121 may be driven by the air to flow from the receiving space 140, through the guiding groove 1322, the through hole 131*c* and the air outlet 131*b*, to reach the smoke outlet 112. In the present embodiment, the air vent 14*b* may be an integrated unobstructed hole, a cross-sectional area of the air vent 14*b* may be greater than a sum of cross-sectional areas of the plurality of air entering holes 14*a*.

Further, support stages 1421 may be formed oppositely on each of the two side walls 142. When the lid 13 is received in the receiving space 140 of the base 14 and fix with the two side walls, the support stages 1421 may support the housing portion 132 of the lid 13. For example, when the first sealing member 15 encases the porous ceramic liquid guiding member 121, and when the porous ceramic liquid guiding member 121 is fixed between the lid 13 and the base 14, an end of the first sealing member 15 may be arranged between the top face 121*a* of the porous ceramic liquid guiding member 121 and the bottom 1312 of the guiding portion 131, and the other end of the first sealing member 15 may further be arranged between the support stages 1421 and the porous ceramic liquid guiding member 121, to achieve the sealing. In the present embodiment, the first sealing member 15 may be made of silicone or the like, and formed as an integral component.

A first situation of the air guiding channel 16 of the present embodiment may be described herein.

Referring to FIG. 2 to FIG. 5, alternatively, the first sealing member 15 may include a top wall 151, arranged to surround the liquid guiding groove 1211, encasing the top face of the porous ceramic liquid guiding member 121, and supporting the lid 13, but the liquid guiding groove 1211 may be exposed. A bottom face of the top wall 151, facing the porous ceramic liquid guiding member 121, and the porous ceramic liquid guiding member 121 may define the air guiding channel 16. For example, the bottom face of the top wall 151 may be a gasket, surrounding the liquid guiding groove 1211 and contacting the top face of the porous ceramic liquid guiding member 121. In such a way, the top wall 151 may contact the top face of the porous ceramic liquid guiding member 121 and the bottom face of the guiding portion 131 to achieve the sealing. That is the first sealing member 15 may define a hole corresponding to the liquid guiding groove 1211.

Figure 5:
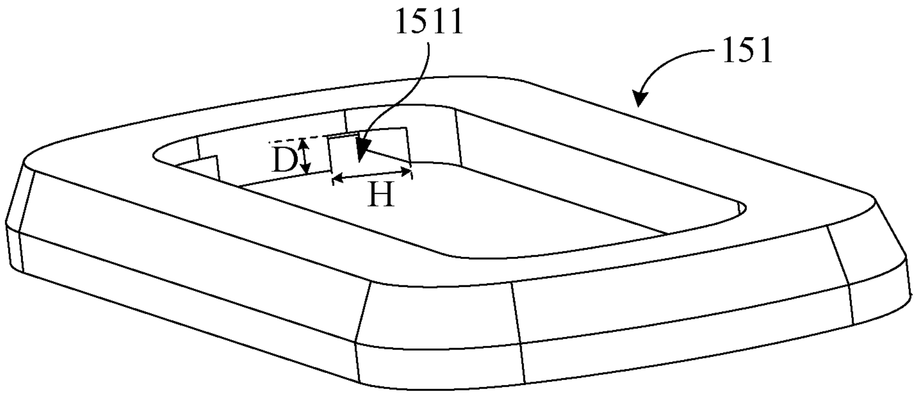
FIG. 5 is a perspective view of a first sealing member in a first situation according to an embodiment of an atomization device in the present disclosure.

Referring to FIG. 5, alternatively, the bottom face of the top wall 151 facing the porous ceramic liquid guiding member 121 may define a first air guiding recess 1511. When the first sealing member 15 is engaged with the porous ceramic liquid guiding member 121, the top face 121*a* of the porous ceramic liquid guiding member 121 may support the bottom face of the top wall 151, therefore, the first air guiding recess 1511 may function as the air guiding channel 16. In order to define the air guiding channel 16, the bottom face of the top wall 151, facing the porous ceramic liquid guiding member 121, may define at least one of the first air guiding recesses 1511, which may be striped recesses. When the first sealing member 15 seals the porous ceramic liquid guiding member 121, there may be gaps between the inner side face of the top wall 151 and the top face 121*a* of the porous ceramic liquid guiding member 121, wherein the gaps may function as the air guiding channels 16. The air entering from the air entering hole 14*a* of the base 14 may flow along the air guiding channel 16 to reach the liquid inlet 131*a* defined on the lid 13, further reaching the liquid cavity 111, to balance the inner pressure of the liquid cavity 111 with the outside, such that liquid may be prevented from being obstructed.

Alternatively, a depth D of the first air guiding recess 1511 may be 0.1 mm-0.3 mm. Alternatively, the depth D of the first air guiding recess 1511 may be 0.15 mm-0.25 mm. Alternatively, a width H of the first air guiding recess 1511 may be 0.5 mm-1 mm. Alternatively, the width H of the first air guiding recess 1511 may be 0.7 mm-0.8 mm. In the present embodiment, the depth D may refer to a distance between a side wall of the first air guiding recess 1511, facing the bottom face of the top wall 151, and the bottom face of the top wall 151. The width H of the first air guiding recess 1511 may refer to a distance between two opposite side walls of the first air guiding recess 1511, and both of the two opposite side walls of the first air guiding recess are perpendicular to the bottom face of the top wall 151. By defining the first air guiding recess 1511 with such depth D and such width H, the air guiding channel 16 may be defined to allow the air to flow, such that leakage of the liquid may be reduced.

On the basis of the first situation, the first sealing member 15 may be further described hereafter, and a second situation of the air guiding channel 16 of the present embodiment may also be described.

Figure 6:
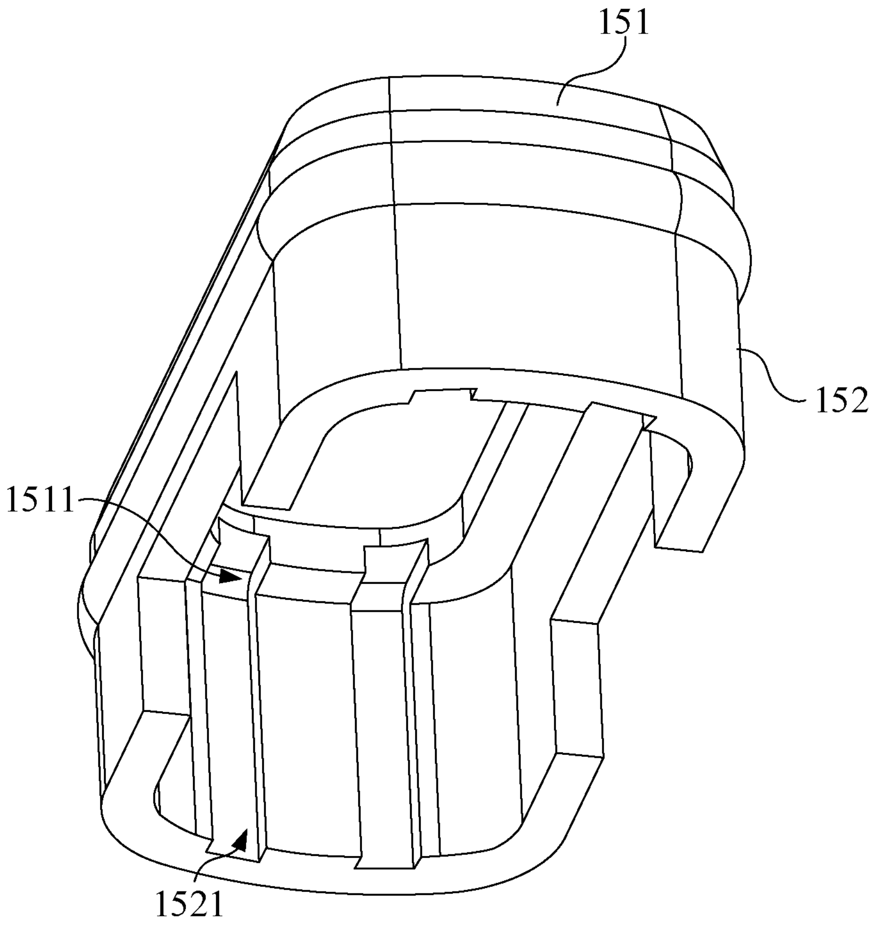
FIG. 6 is a perspective view of a first sealing member in a second situation according to an embodiment of an atomization device in the present disclosure.

Referring to FIG. 6, the first sealing member 15 may be provided to be a case, including a side wall 152 extending from outer edges of the top wall 151. The first sealing member 15 may encase the porous ceramic liquid guiding member 121 and support the lid 13 to achieve the sealing. The side wall 152 may cover at least a portion of the outer side surface 121*c* of the porous ceramic liquid guiding member 121. To be specific, the side wall 152 of the first sealing member 15 may be perpendicular to the top wall 151. When the first sealing member 15 encases the porous ceramic liquid guiding member 121, the top wall may contact the top face 121*a* of the porous ceramic liquid guiding member 121, and the side wall 152 may contact the outer side surface 121*c*, for sealing. By forming the side wall 152 on the first sealing member 15, the sealing effect of the first sealing member 15 may be increased, and the porous ceramic liquid guiding member 121 may be protected.

Alternatively, an inner side face of the side wall 152, facing the porous ceramic liquid guiding member 121, may define at least one second air guiding recesses 1521, wherein the at least one air guiding recesses 1521 may be striped. The second air guiding recesses 1521 may communicate with the first air guiding recesses 1511, and extend along a direction starting from the top face 121*a* towards the bottom face 121*b*. That is the second air guiding recess 1521 may extend from a first end of the side wall 152 towards a second end of the side wall 152 opposite to the first end, wherein the first end may refer to a position at which the side wall 152 connects with the top wall 151. When the first sealing member 15 encases the porous ceramic liquid guiding member 121 and engages with the housing portion 132 of the lid 13, the first air guiding recess 1511 and the second air guiding recess 1521 may function as the air guiding channel 16. To be specific, the bottom face of the top wall 151 may support the top face of the porous ceramic liquid guiding member 121, and the inner side face of the side wall 152 may support the outer side surface of the porous ceramic liquid guiding member 121, such that the first air guiding recess 1511 and the second air guiding recess 1521 may function as the air guiding channel 16. The air entering from the air entering hole 14*a*, defined on the base 14, may flow through the air guiding channel 16, reaching the liquid cavity 111 to balance the pressure inside and outside the liquid cavity 111.

Alternatively, a depth of the second air guiding recess 1521 may be 0.1 mm-0.3 mm, and a width of the second air guiding recess 1521 may be 0.5 mm-1 mm. Alternatively, the depth of the second air guiding recess 1521 may be 0.15 mm-0.25 mm, and the width of the second air guiding recess 1521 may be 0.7 mm-0.8 mm. Indications of the depth and width of the second air guiding recess 1521 may refer to those of the first air guiding recess 1511.

On the basis of the first and the second situation, the first sealing member 15 and the second air guiding recesses 1521 may be further described hereafter, a third situation of the air guiding channel 16 may be described as following.

Similar to the second situation, the side wall 152 of the first sealing member 15 under the third situation may have a structure different from that under the second situation, description of the first sealing member 15 under the third situation may refer to that under the second situation.

Figure 7:
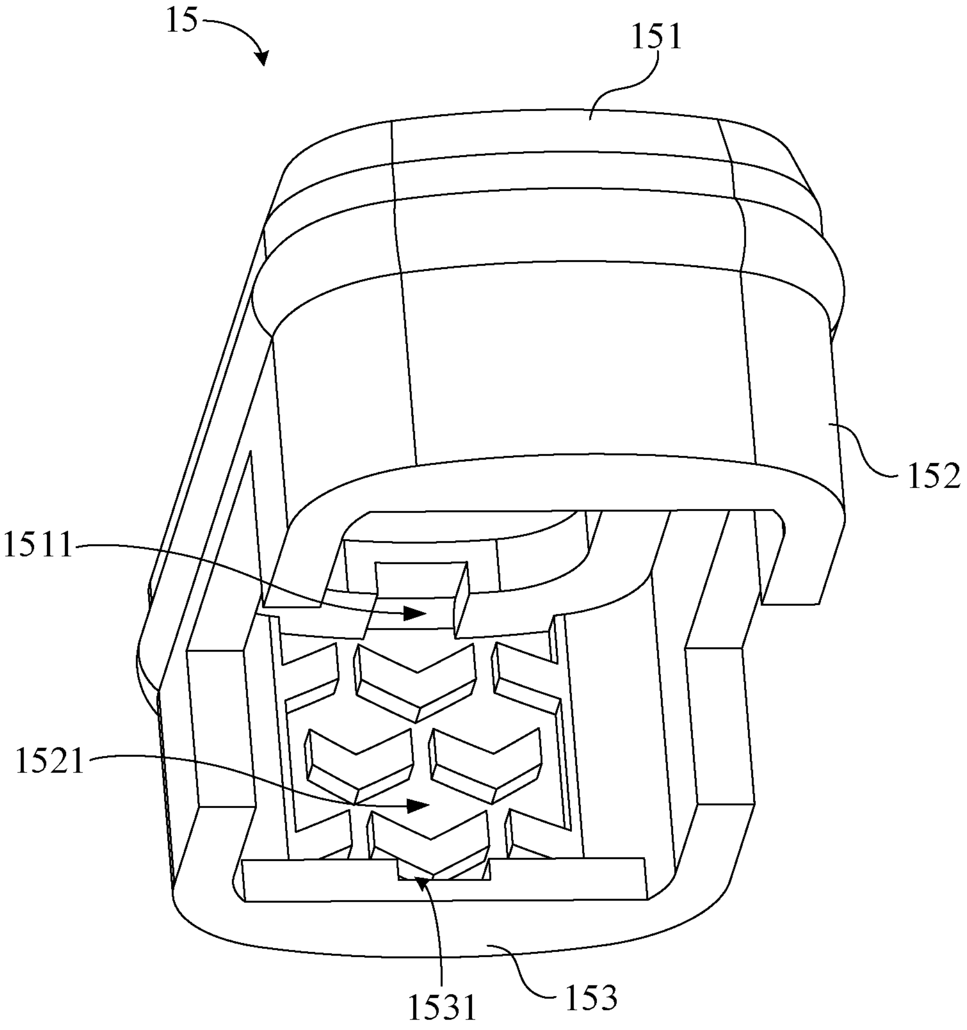
FIG. 7 is a perspective view of a first sealing member in a third situation according to an embodiment of an atomization device in the present disclosure.

Referring to FIG. 7, alternatively, the inner side face of the side wall 152, facing the porous ceramic liquid guiding member 121, may define a second air guiding recess 1521, wherein the second air guiding recess 1521 may be twisted and turned and communicate with the first air guiding recess 1511. When the first sealing member 15 encases the porous ceramic liquid guiding member 121 and engages with the housing portion 132 of the lid 13, the first air guiding recess 1511 and the second air guiding recess 1521 defined may function to be an air guiding channel 16. By defining the second air guiding recess 1521 to be twisted and turned, liquid leakage may be prevented effectively, and longer time may be taken for the liquid to flow, such that the liquid may be sufficiently atomized. Alternatively, the second air guiding recess 1521 may be V-shaped, and a plurality of the V-shaped air guiding recesses 1521 may be inter-communicated. The smoke may rise along the plurality of the V-shaped air guiding recesses. Also, the V shaped recesses may block the liquid leakage to some extent.

On the basis of the second or the third situation, the first sealing member 15 may be further described hereafter, and a fourth situation of the air guiding channel 16 may be described.

Figure 8:
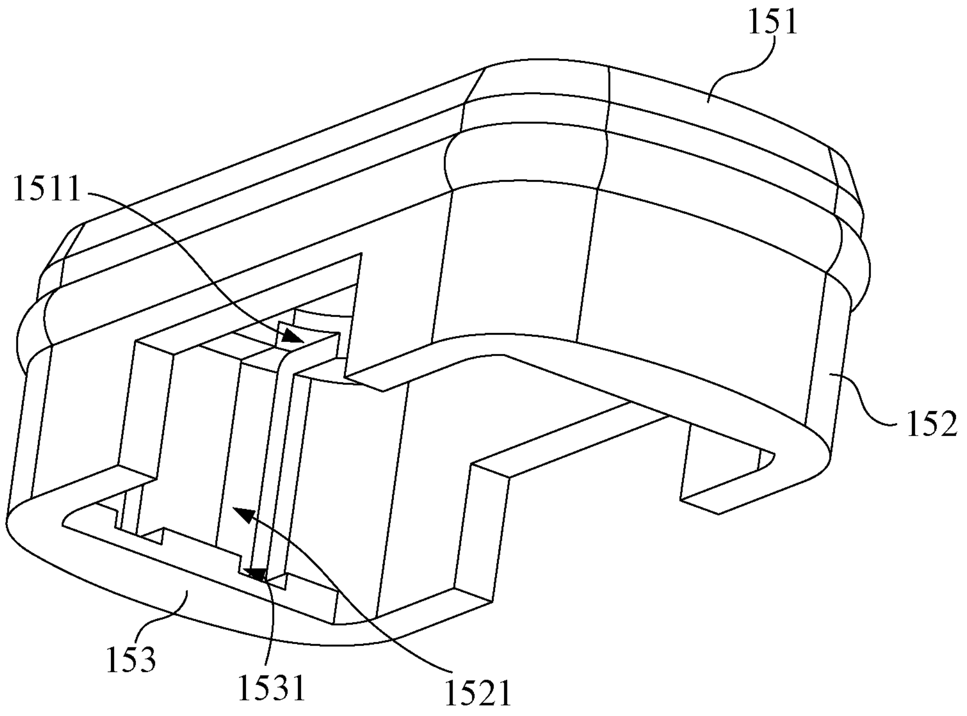
FIG. 8 is a perspective view of a first sealing member in a fourth situation according to an embodiment of an atomization device in the present disclosure.

Referring to FIG. 7 and FIG. 8, alternatively, the first sealing member 15 may further include two bottom walls 153 parallel to the top wall 151, the two bottom walls 153 may be formed oppositely on the first sealing member 15, and each of the two bottom walls 153 may connect with the an end of the side wall 152 away from the top wall 151. The outer side surface 121*c* of the porous ceramic liquid guiding member 121 may be embedded to form a stair face 121*d*. To be specific, when the porous ceramic liquid guiding member 121 is received in the receiving space 140 of the base 14, the stair face 121*d* may be formed on the outer side surface 121*c* of the porous ceramic liquid guiding member 121, facing the side wall 142. A direction towards which the stair face 121*d* is facing is opposite to a direction towards which the opening of the porous ceramic liquid guiding member 121 is facing, that is the stair face 121*d* is facing to a direction of where the bottom face 121*b* is arranged. When the first sealing member 15 encases the porous ceramic liquid guiding member 121, the bottom wall 153 may cover and surround the stair face 121*d*, and further contact the support stage 1421 of the base 14, such that the stair face 121*d* may be sealed. The formation of the bottom wall 153 may improve the sealing effect of the first sealing member 15, and encasing a portion of the porous ceramic liquid guiding member 121 by the top wall 151, the side wall 152 and the bottom wall 153 may firm the engagement between the first sealing member 15 and the porous ceramic liquid guiding member 121.

Referring to FIG. 7 and FIG. 8, alternatively, an inner face of the bottom wall 153, facing the stair face, may define at least one third air guiding recess 1531. Each third air guiding recess 1531 may communicate with at least one of the second air guiding recesses 1521 and the receiving space 140 defined by the base 14. Engagement of the porous ceramic liquid guiding member 121 with the first sealing member 15 may allow the third air guiding recess 1531, the second air guiding recesses 1521, and the first air guiding recesses 1511 to function to be the air guiding channel 16. The receiving space 140 defined by the base 14 may receive the external air flowing through the air entering hole. To be specific, the third air guiding recess 1531 may communicate with the second air guiding recesses 1521 as described in the second and/or third situations. When the first sealing member 15 encases the porous ceramic liquid guiding member 121, the third air guiding recesses 1531, the second air guiding recesses 1521, and the first air guiding recesses 1511 may inter-communicated, and the engagement of the porous ceramic liquid guiding member 121 with the first sealing member 15 may allow the intercommunicated air guiding recesses to function as the air guiding channel 16, external air entering from the air entering hole 14*a* may flow through the air guiding channel 16 to reach the liquid cavity 111.

A depth of the third air guiding recesses 1531 may be 0.1 mm-0.3 mm, alternatively, the depth may be 0.15 mm-0.25 mm. A width of the third air guiding recesses 1531 may be 0.5 mm-1 mm, alternatively, the width may be 0.7 mm-0.8 mm. The indications of the depth and the width of the third air guiding recesses may refer to those descried for the first situation.

A fifth situation of the air guiding channel 16 may be described hereafter.

Figure 9:
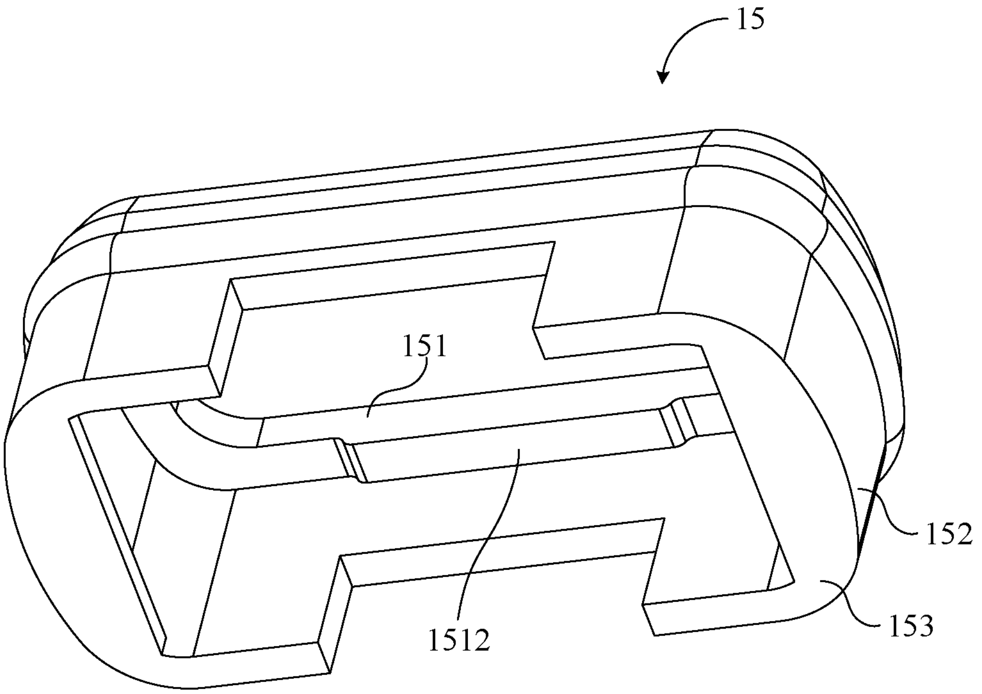
FIG. 9 is a perspective view of a first sealing member in a fifth situation according to an embodiment of an atomization device in the present disclosure.

Referring to FIG. 9, a protruded stage 1512 may be formed on the bottom face of the top wall 151 facing the porous ceramic liquid guiding member 121, and support the top face 121*a* of the porous ceramic liquid guiding member, such that gaps may be defined between the bottom face of the top wall 151 and the top face 121*a* of the porous ceramic liquid guiding member 121, and may function as the air guiding channel 16. To be specific, more than one protruded stages 1512 may be formed on the bottom face of the top wall 151 facing the porous ceramic liquid guiding member 121. For example, two protruded stages 1512 may be formed on two opposite bottom faces separately. When the first sealing member 15 engaged between the bottom face of the guiding portion 131 and the top face 121*a* of the porous ceramic liquid guiding member 121, the protruded stages 1512 which are formed by protruding from the bottom face of the top wall 151 may cause the bottom face of the top wall 151 and the top face 121*a* of the porous ceramic liquid guiding member 121 to define gaps, wherein the gaps may function as the air guiding channel 16.

Alternatively, a length of where the protruded stage 1512 protruding from the bottom face of the top wall 151 may be 0.1 mm-0.2 mm. Further, under the fifth situation, when the first sealing member 15 includes the side wall 152 and the bottom wall 153, it may be unnecessary for the side wall 152 and the bottom wall 153 to define another protruded stage 1512.

Figure 10:
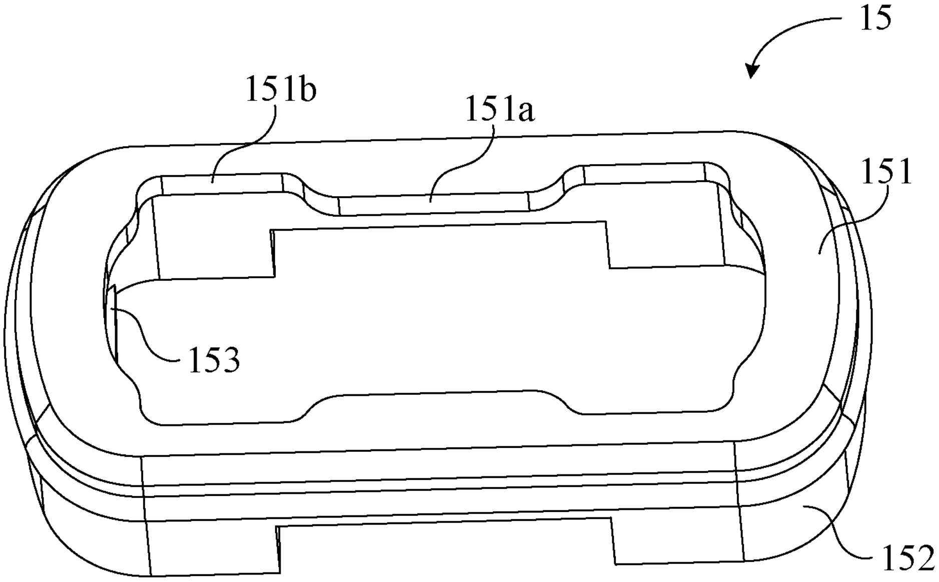
FIG. 10 is another perspective view of a first sealing member according to an embodiment of an atomization device in the present disclosure.

Referring to FIG. 10, in the present embodiment, an inner edge of the top wall 151 may be uneven, having a protruded portion 151*a* and a recessing portion 151*b*, and the protruded portion 151*a* may protrude from the inner edge of the top wall 151. The uneven inner edge of the top wall 151 may stable the engagement between the first sealing member 15 and the porous ceramic liquid guiding member 121, and increase an exposure area of the top face 121*a* of the porous ceramic liquid guiding member 121, such that a larger porous structure of the porous ceramic liquid guiding member 121 may be exposed to ease the air flow into the liquid cavity 111.

In other embodiments, the air guiding channel 16 may be defined by curved surfaces of the first sealing member 15, wherein the air guiding channel may be generated by compression. To be specific, during engagement, the porous ceramic liquid guiding member 121 and the lid 13 may compress and deform the first sealing member 15, such that inner surfaces of the first sealing member 15 facing the porous ceramic liquid guiding member 121 may be curved, the air guiding channel 16 may be defined by the curved inner surfaces of the first sealing member 15 and the porous ceramic liquid guiding member 121.

In other embodiments, the air guiding channel 16 may be defined on a surface of the porous ceramic liquid guiding member 121, wherein the surface contacts the first sealing member 15. For example, the surface of the porous ceramic liquid guiding member 121 contacting the first sealing member 15 may define a slot (not shown in the figure). When the porous ceramic liquid guiding member 121 is engaged with the first sealing member 15, side walls of the slot may support the first sealing member 15 to define the air guiding channel 16.

Figure 11:
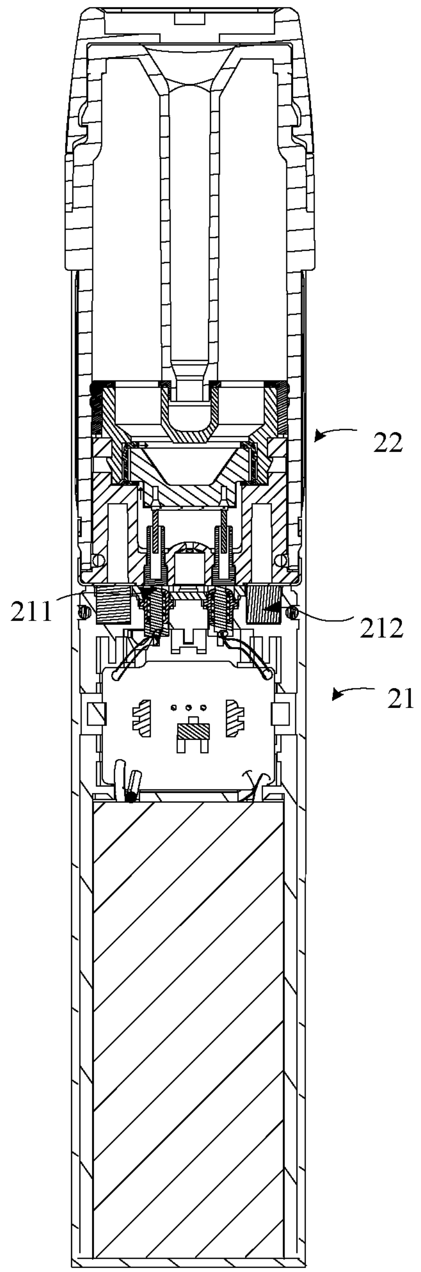
FIG. 11 is a schematic view of the electronic atomization device taken from the line II-II of the embodiment shown in FIG. 1.

As shown in FIG. 11, an electronic atomization device may be provided according to an embodiment of the present disclosure. The electronic atomization device may include a power assembly 21 and an atomizer 22 as described in an embodiment of the atomization device. The power assembly 21 may be configured to supply power to the atomization device for working, such that a liquid may be atomized to generate a smoke.

Detailed structure of the atomization device may refer to the above-mentioned embodiments of the present disclosure, and will not be repeatedly described hereafter.

To be specific, the power assembly 21 may include at least two power contacts 211, and an electrode hole mount may be arranged on the base of the electronic atomization device. The at least two power contacts may be configured to contact a contact of the electrode hole mount, such that power may be supplied to the atomizer 22. The power assembly may include for instance a battery. Further, the power assembly may include a magnetic element 212, wherein the magnetic element 212 may be arranged to magnetically attract the atomizer 22, such that the atomizer 22 may be fixedly connected to the power assembly 21.

FIGS. 12 to 19 may illustrate other embodiments of the atomizer of the present disclosure, and will be described in details in following paragraphs.

Figure 12:
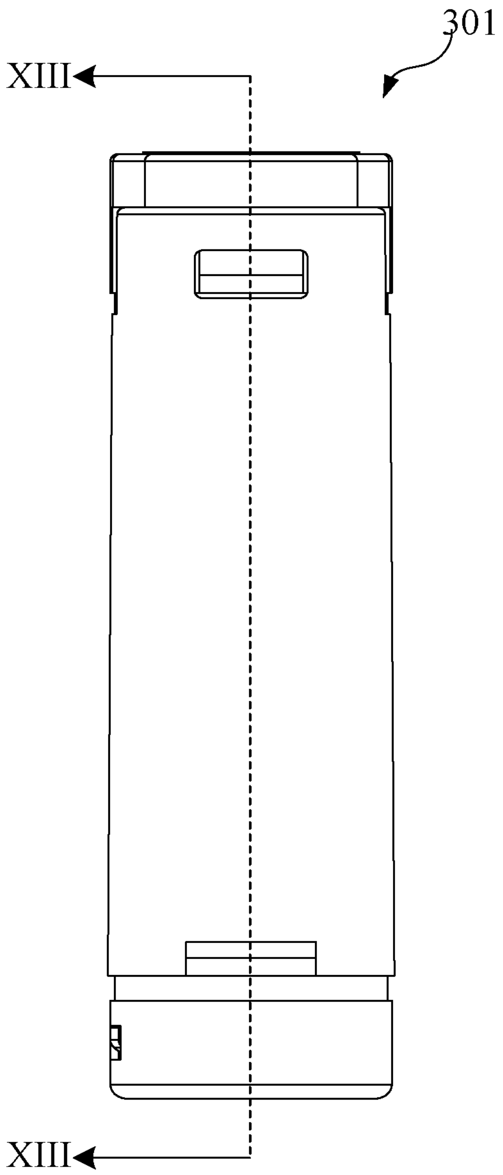
FIG. 12 is a side view of an electronic atomization device according a first embodiment of the present disclosure.
Figure 13:
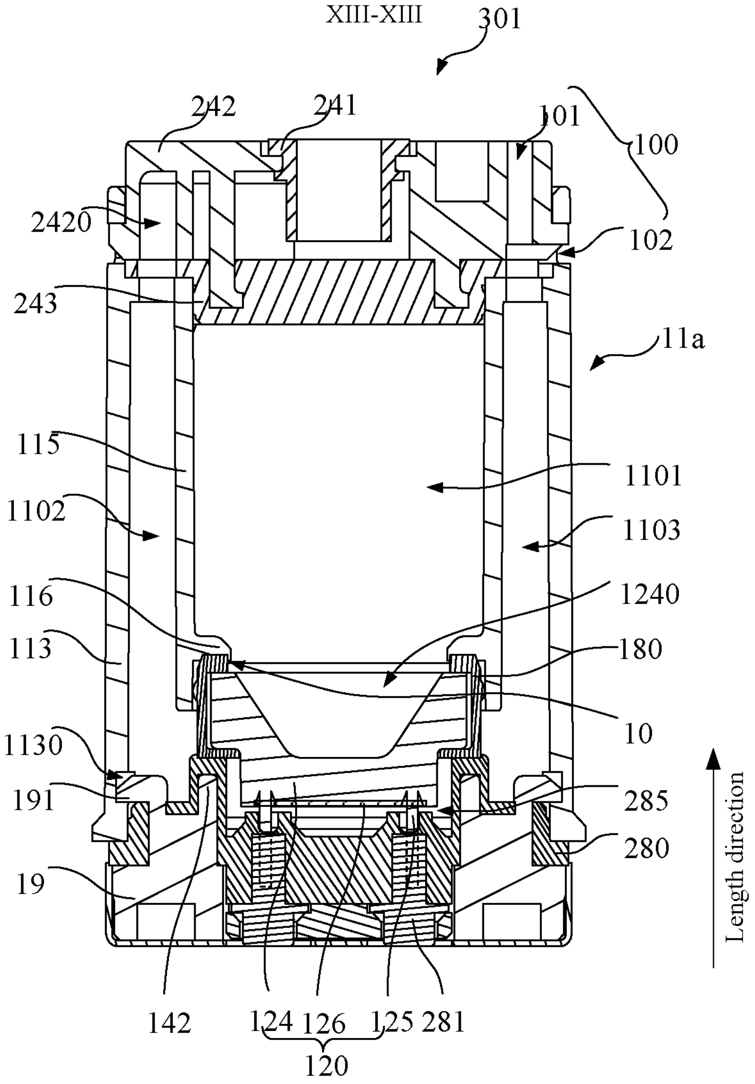
FIG. 13 is a schematic view taken from the line XIII-XIII of the embodiment shown in FIG. 12.

As shown in FIG. 12 and FIG. 13, the atomizer 301 of an embodiment of the present disclosure may include a tube wall 11*a*, a heating assembly 120, and a first sealing member 180.

The tube wall 11*a* may define a liquid cavity 1101 for storing a liquid. The heating assembly 120 may be arranged to atomize the liquid flowing from the liquid cavity 1101 to generate the smoke. For example, the liquid cavity 1101 and a space defined by the heating assembly 120 may be communicated. Therefore, the liquid stored in the liquid cavity 1101 may flow to reach the heating assembly 120, and the heating assembly 120 may be heated by electric current to atomize the liquid, generating the smoke. The first sealing member 180 may be arranged between the tube wall 11*a* and the heating assembly 120 for sealing. This is to reduce a possibility of the liquid leaking from a gap between the liquid cavity 1101 and the heating assembly 120 during flowing. In the present embodiment, an air guiding channel 10 may be defined between the first sealing member 180 and the tube wall 11*a*, and the first sealing member may achieve the sealing and, at the same time, guide air to flow into the liquid cavity 1101.

According to the present embodiment, by defining the air guiding channel between the first sealing member 180 and the tube wall 11*a*, the air may be easily guided to reach the liquid cavity 1101, such that pressure inside the liquid cavity 1101 may be balanced with an outside, and obstructed flow of the liquid caused by negative pressure of the liquid cavity 1101 may be solved, improving user experience and simplifying a structure of the atomizer.

Figure 14:
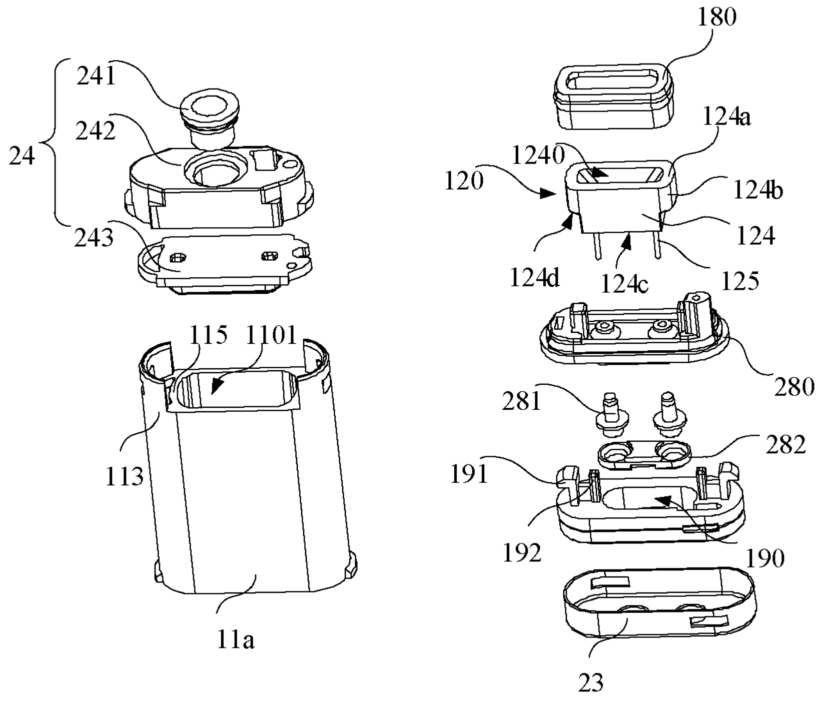
FIG. 14 is an isometric view taken from the line XIII-XIII of the embodiment shown in FIG. 12.

Further as shown in FIGS. 12 to 14, in the present embodiment, the tube wall 11*a* may include a first tube wall 115, wherein the first tube wall may define the liquid cavity 1101, and the liquid may be stored in the liquid cavity 1101 defined by the first tube wall 115.

Alternatively, the tube wall 11*a* may be arranged to be tubular, or a shape of the tube wall may be designed according to actual demands. The tube wall 11*a* may define the liquid cavity 1101, a smoke outlet 1101, and an air entering channel 1103, wherein each of the liquid cavity 1101, the smoke outlet 1101, and the air entering channel 1103 may extend along a length direction of the tube wall 11*a*. The liquid cavity 1101, the smoke outlet 1101, and the air entering channel 1103 may be defined spaced apart from each other, for example, they are not communicated directly within the tube wall 11*a*.

For example, the tube wall 11*a* may include a first tube wall 115 and two second tube walls 113. The first tube wall 115 may define a liquid cavity 1101. Each of the two second tube walls 113 may be bent at one end, and connected to the first tube wall 115 at the bent end. One of the two second tube walls 113 may be connected to a side of the first tube wall 115 to define the smoke outlet 1102, and the other of the two second tube walls 113 may be connected to an opposing side of the first tube wall 115 to define the air entering channel 1103. In the present embodiment, the air entering channel 1103 may be defined to guide the external air to flow to a position at which the heating assembly 120 is located, and an air flow generated by the external air may drive the smoke generated by the heating assembly 120 to flow into the smoke outlet 1102, such that the smoke may be guided to flow through the smoke outlet 1102 to reach a component, such as a mouthpiece, and may be inhaled by the user.

For example, the atomizer 310 may further define an air entering hole 100 communicating with the air entering channel 1103. The air out of the atomizer 301 may enter the air entering channel 1103 through the air entering hole 100.

To be specific, the second tube walls 113 may be arranged at two opposing sides of the first tube wall 115. The first tube wall 115 may be arranged between the smoke outlet 1102 and the liquid cavity 1101, such that the smoke outlet 1102 and the liquid cavity 1101 are not directly communicated. The first tube wall 115 may further be arranged between the liquid cavity 1101 and the air entering channel 1103, such that the liquid cavity 1101 and the air entering channel 1103 are not directly communicated. Alternatively, the tube wall 11*a* may be manufactured as an integral component, and that is the first tube wall 115 and the two second tube walls 113 may be an integral component. In the present embodiment, along the length direction of the tube wall 11*a*, a length for which the second tube wall 113 extends may be greater than a length for which the first tube wall 115 extends.

In the present embodiment, the heating assembly 120 may be partially received in a space defined by the first tube wall 115. For example, the heating assembly 120 may be embedded into an end of the liquid cavity 1101. The first sealing member 180 may abut against an inner surface of the first tube wall 115 and an outer surface of the heating assembly 120 for sealing. An air guiding channel 10 may be defined between the first sealing member 180 and the first tube wall 115. For example, a protrusion may be arranged on the inner surface of the first tube wall 115 facing towards the heating assembly 120, alternatively, a recess may be defined in the inner surface of the first tube wall 115 facing towards the heating assembly 120. When the first sealing member 180 abuts against the inner surface of the first tube wall 115, a gap may be defined between the first sealing member 180 and the first tube wall 115 due to the protrusion or the recess, and the gap may function as the air guiding channel 10.

Alternatively, the entire heating assembly 120 may be arranged beneath the first tube wall 115, and the first sealing member 180 may be arranged to be various shapes, with a proviso that the liquid cavity 1101 communicates with the space defined by the heating assembly 120. In the present embodiment, the first sealing member 180 may abut between the first tube wall 115 and the heating assembly 120 for sealing, and the air guiding channel 10 may be defined by arranging the protrusion or defining the recess between the first sealing member 180 and the first tube wall 115.

Figure 15:
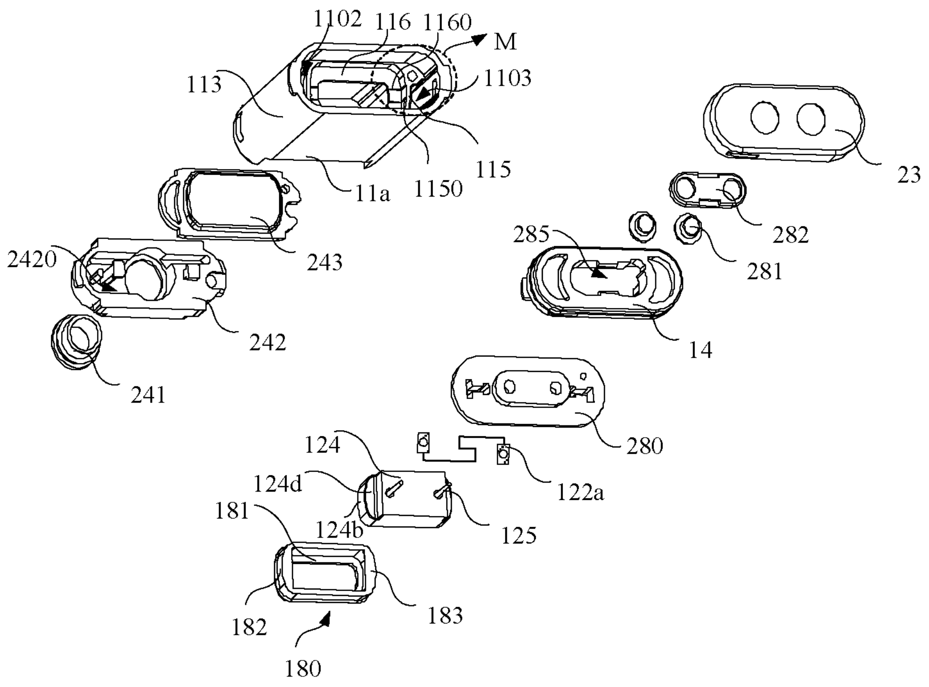
FIG. 15 is another isometric view of the embodiment shown in FIG. 12.
Figure 16:
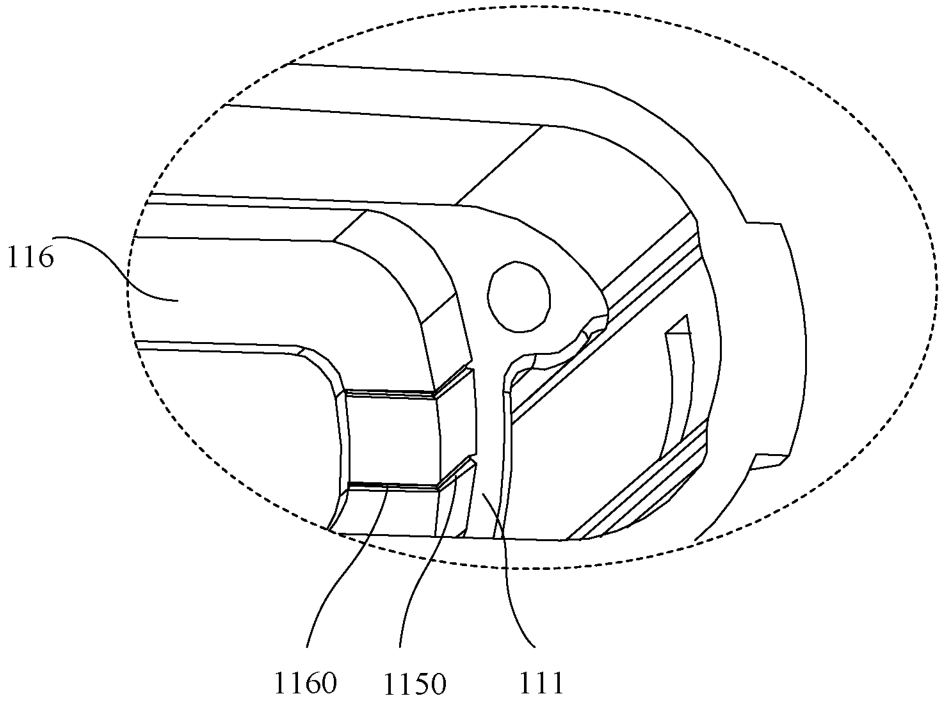
FIG. 16 is an enlarged view of an M portion of the structure shown in FIG. 15.

As shown in FIGS. 14 to 16, in the present embodiment, the inner surface of the first tube wall 115 facing towards the heating assembly 120 may be arranged with a plurality of first convex ribs 1150, wherein the plurality of first convex ribs 1150 may protrude from the inner surface of the first tube wall 115. When the first sealing member 180 abuts against the plurality of first convex ribs 1150, the air guiding channel 10 may be defined between the inner surface of the first tube wall 115 and the first sealing member 180. To be specific, when the first sealing member 180 abuts against the inner surface of the first tube wall 115, as the plurality of first convex ribs 1150 protrudes from the inner surface of the first tube wall 115, a gap may be defined between each of the plurality of first convex ribs 1150, and the gap may serve as the air guiding channel 10.

Alternatively, as shown in FIG. 13 and FIG. 15, the inner surface of the first tube wall 115 facing towards the heating assembly 120 may be arranged with a flange 116 along a circumferential direction. The flange 116 may be arranged to abut against the heating assembly 120, and may allow the sealing between the flange 116 and the heating assembly 120. The first sealing member 180 may be clamped between the flange 116 and the heating assembly 120, and contact the flange 116 and the heating assembly 120 at the same time for sealing, such that the liquid may be protected from leaking during flowing from the liquid cavity 1101 to the heating assembly 120. In the present embodiment, the flange 116 may be formed on the inner surface of the first tube wall 115, and the flange 116 and the first tube wall 115 may be an integral component. In other embodiments, the tube wall 11*a* including the second tube wall 113, the first tube wall 115, and the flange 116 may not be an integral component. The flange 116 may be arranged on the inner surface of the first tube wall 115 in a detachable manner. An outer edge of the flange 116 may define a hole, and that means a middle portion of the flange 116 may be porous, such that the liquid may flow from the liquid cavity 1101 through the hole to reach the heating assembly 120. In the present embodiment, the air guiding channel 10 may be defined between the first sealing member 180 and the inner surface of the first tube wall 115, and defined between the first sealing member 180 and the flange 116. In the present embodiment, the external air may enter the liquid cavity 1101 through the air guiding channel 10, such that, to some extent, the pressure inside the liquid cavity 1101 may be balanced with the outside of the liquid cavity 1101.

In the present embodiment, when the atomizer 301 is working, for example, when a user is inhaling, the inhalation may generate a pressure, and the pressure may enable the air to enter the atomizer 301 through the air entering hole 100, generating an air flow inside the atomizer 301. The liquid may flow to the heating assembly 120 and may be atomized to generate the smoke. The smoke may be driven by the air flow to flow into the smoke outlet 1102 and reach the user to be inhaled. As the air guiding channel 10 may guide the air to flow into the liquid cavity 1101. A pressure difference between the inside and the outside of the liquid cavity 1101 may be decreased, such that a negative pressure generated due to consumption of the liquid stored in the liquid cavity 1101 may be reduced, and the liquid may flow downwards smoothly, and a burnt taste of the electronic atomization device may be reduced, improving user experience.

As shown in FIG. 13, alternatively, the flange 116 may protrude towards a direction perpendicular to the inner surface of the first tube wall 115, wherein the inner surface is facing towards the heating assembly 120, or the flange 116 may protrude towards a direction perpendicular to the length direction of the tube wall 11*a*.

As shown in FIG. 15 and FIG. 16, alternatively, the flange 116 may be arranged with a plurality of second convex ribs 1160 on a surface of the flange 116 facing towards the first sealing member 180. The plurality of second convex ribs 1160 may be spaced apart from each other and arranged to protrude from the surface of the flange 116. When the first sealing member 180 abuts against the plurality of second convex ribs 1160, protrusion of the plurality of second convex ribs 1160 allows the plurality of second convex ribs 1160 to have a height, the height allows a gap to be defined between the flange 116 and the first sealing member 180, and the gap may at least be defined near the plurality of first convex ribs 1150. As the first sealing member 180 abuts against the flange 116, the inner surface of the first tube wall 115, and the heating assembly 120, gaps defined near the plurality of first convex ribs 1150 and near the plurality of second convex ribs 1160 may be inter-communicated, and the gaps may serve as the air guiding channel 10. In such a way, the air may smoothly flow into the liquid cavity 1101 through the air guiding channel 10.

In the present embodiment, the plurality of first convex ribs 1150 and the plurality of second convex ribs 1160 may be formed on the tube wall 11*a* as an integral component. Protrusion of the plurality of first convex ribs 1150 from the inner surface of the first tube wall 115 and protrusion of the plurality of second convex ribs 1160 from the flange 116 may be easily molded together with the tube wall 11*a*.

For example, during assembling, the first sealing member 180 may encase an outer circumference of the heating assembly 120, and the heating assembly 120 encased with the first sealing member 180 may be embedded into the space defined by the first tube wall 115 from an end of the first tube wall 115 close to the flange 116. The first sealing member 180 may contact the inner surface of the first tube wall 115 and the flange 116 at the same time, such that the first tube wall 115 may be sealed with the heating assembly 120 effectively. Due to the height of the plurality of first convex ribs 1150, a gap may be defined between the first sealing member 180 and the inner surface of the first tube wall 115, the gap may at least be defined near the plurality of first convex ribs 1150. By arranging the plurality of first convex ribs 1150 and the plurality of second convex ribs 1160 cooperatively, the gap defined between the first sealing member 180 and the inner surface of the first tube wall 115 facing towards the heating assembly 120 and the gap defined between the first sealing member 180 and the flange 116 may serve as the air guiding channel 10. The air may smoothly enter the liquid cavity 1101 through the air guiding channel 10. According to the present embodiment, by arranging the plurality of first convex ribs 1150 and the plurality of second convex ribs 1160, the air guiding channel 10 may be defined effectively, such that the air may smoothly enter the liquid cavity 10, the pressure inside the liquid cavity 1101 may be balanced with the outside, and a possibility of obstructed liquid flow may be reduced.

Further referring to FIG. 15 and FIG. 16, alternatively, an end of the a second convex rib 1160 may extend to the outer edge of the flange 116, and an opposing end of the second convex rib 1160 may extend to an intersection at which the flange 116 is connected to the first tube wall 115. For example, the second convex rib 1160 may be substantially linear. An end of a first convex rib 1150 may be connected to the opposing end of the second convex rib 1160, and an opposing end of the first convex rib 1150 may extend an edge of the first tube wall 115 close to the heating assembly 120. The first convex rib 1150 may be substantially linear. In the present embodiment, the second convex rib 1160 may be connected to the first convex rib 1150, such that the air may flow along the air guiding channel 10 more smoothly. In other embodiments, a shape of the second convex rib 1160 and a shape of the first convex rib 1150 may be curved or arched, and will not be limited. In other embodiments, the second convex rib 1160 and the first convex rib 1150 may be arranged spaced apart from each other. For example, an end of the second convex rib 1160 at the intersection of which the flange 116 is connected to the first tube wall 115 and an end of the first convex rib 1150 at the intersection of which the flange 116 is connected to the first tube wall 115 may be disconnected.

Further referring to FIG. 5, alternatively, 2 to 8 first convex ribs 1150 may be arranged on two opposing sides of the inner surface of the first tube wall 115, and the first convex ribs 1150 arranged on a same side may be spaced apart from each other. For example, there may be four first convex ribs 1150 arranged on two sides of the inner surface of the first tube wall 115, two first convex ribs 1150 may be arranged on each of the two sides, and the two first convex ribs 1150 which are arranged on a same side may be spaced apart from each other. A distance between the two first convex ribs 1150 arranged on the same side may be 1-3 mm, wherein the distance may be determined according to actual demands.

Further referring to FIG. 15, alternatively, 2 to 8 second convex ribs 1150 may be arranged on two opposing sides of the surface of the flange 116, wherein the surface is facing towards the heating assembly 120. Some of the second convex ribs 1160 may be arranged on one of the two opposing sides, and the other of the second convex ribs 1160 may be arranged on the other of the two opposing sides. For example, there may be four second convex ribs 1160 arranged, two of the four second convex ribs 1160 may be arranged on one of the two opposing sides, and the other two of the four second convex ribs 1160 may be arranged on the other of the two opposing side. The two second convex ribs 1160 which are arranged on a same side may be spaced apart from each other. A distance between the two second convex ribs 1160 arranged on the same side may be 1-3 mm, wherein the distance may be determined according to actual demands. The number of the first convex ribs 1150 and the number of the second convex ribs 1160 may be of equal or different. For example, four first convex ribs 1150 and four second convex ribs 1160 may be arranged, and the four first convex ribs 1150 may be connected to the four second convex ribs 1160 correspondingly.

In other embodiments, the second convex rib 1160 may be arranged on a surface of the flange 116 facing towards the first sealing member 180, but may not be connected to the intersection of the flange 116 and the first tube wall 115, and may not be connected to the inner edge of the flange 116. However, the second convex rib 1160 may not be arranged to be a closed loop, as the closed loop may block the air flow, and the liquid cavity 1101 may not be able to communicate with the outside. To be specific, the second convex rib 1160 may be arranged on the surface of the flange 116 facing towards the first sealing member 180, and a shape and an extension direction of the second convex rib 1160 may not be limited. A first end of the second convex rib 1160 may be arranged at any position of the surface of the flange 116 facing towards the first sealing member 180, but may be not connected to the intersection of the flange 116 and the first tube wall 115, and may not be connected to the inner edge of the flange 116. A second end of the second convex rib 1160 may be arranged at any position of the surface of the flange 116 facing towards the first sealing member 180, but may be not connected to the intersection of the flange 116 and the first tube wall 115, may not be connected to the inner edge of the flange 116, and may not be connected to the first end of the second convex rib 1160. In such a way, a closed loop may not be formed. Similarly, the first convex rib 1150 may be arranged on the inner surface of the first tube wall 115, but may not be connected to the intersection of the flange 116 and the first tube wall, and may not be connected to any edge of the first tube wall. In addition, two ends of the first convex rib 1150 may not be connected to each other, such that a closed loop may not be formed.

In other embodiments, the first convex rib 1150 may be arranged on a surface of the first sealing member 180 facing towards the first tube wall 115. Further, the second convex rib 1160 may be arranged on a surface of the first sealing member 180 facing towards the flange 116. In some other embodiments, the first convex rib 1150 may be arranged on the surface of the first sealing member 180 facing towards the first tube wall 115, and the second convex rib 1160 may be arranged on the surface of the flange 116 facing towards the first sealing member 180. Alternatively, the first convex rib 1150 may be arranged on the inner surface of the first tube wall 115, and the second convex rib 1160 may be arranged on the surface of the first sealing member 180 facing towards the flange 116. When the first sealing member 180 abuts against the first tube wall 115 and the flange 116, a gap defined near the first convex rib 1150 and a gap defined near the second convex rib 1160 may be communicated and serve as the air guiding channel 10.

Further referring to FIGS. 13 to 15, alternatively, the heating assembly 120 may include a porous ceramic liquid guiding member 124 and a heating member 122*a*. In the present embodiment, the porous ceramic liquid guiding member 124 may be made of ceramic or the like. The ceramic may contain aggregates, binders, and pore-forming agents, and undergo a sintering process. A plurality of pores may be defined within the ceramic, communicating with each other and with surfaces of the ceramic. The ceramic may have high porosity, be chemically stable, and have a large specific surface area, a small volumetric density, a low thermal conductivity, corrosion and thermal resistance. The porous and twisted structure inside the porous ceramic liquid guiding member 124 may cause an ineffective air flow and an ineffective flow of the liquid downwards. Therefore, in the present embodiment, by defining the air guiding channel 10, the air may smoothly flow through the air guiding channel to reach the liquid cavity 1101 to reduce the negative pressure caused by inhalation of the user, and the ineffective downward flow the liquid may be reduced, further reducing a burnt taste, improving an efficiency of atomization of the atomizer 301, and improving user experience.

Further referring to FIG. 13 and FIG. 14, a side face of the porous ceramic liquid guiding member 124 facing towards the liquid cavity 1101 may define a liquid guiding groove 1240. That is to say the liquid guiding groove 1240 may be defined by the side face (a top face 124*a*) of the porous ceramic liquid guiding member 124 facing towards the liquid cavity 1101 being recessed inwardly away from the liquid cavity 1101. A plurality of cross sections may be obtained from the porous ceramic liquid guiding member 124, each of plurality of cross sections is in parallel with the top face 124*a*, and areas of the plurality of cross sections may gradually decrease along a depth direction of the liquid guiding groove 1240. The liquid guiding groove 1240 may be defined to receive the liquid flowing from the liquid cavity 1101, and the liquid may flow through the porous structure to reach the heating member 122*a*. In the present embodiment, by defining the liquid guiding groove 1240, the liquid may be received, and a contact area between the liquid and the porous ceramic liquid guiding member 124 may be increased, and flowing efficiency and a flowing speed of the liquid may be improved.

Alternatively, an outer surface 124*b* of the porous ceramic liquid guiding member 124 may have two opposing sides, each of the two opposing sides may be arranged with a stage, and the stage may have a stage face 124*d* opposite to the top face 124*a*. When the first sealing member 180 encases the porous ceramic liquid guiding member 124, an edge of the top face 124*a*, a part of the outer surface 124*b*, and the stage face 124*d* may be covered, such that sealing may be achieved effectively when the porous ceramic liquid guiding member 124 is embedded into the space defined by the first tube wall 115.

Further referring to FIGS. 13 to 15, the first sealing member 180 may be a case, including a top wall 181. The top wall 181 may be arranged between the top face 124*a* of the porous ceramic liquid guiding member 124 and the flange 116, surrounding the liquid guiding groove 1240, covering the top face 124*a*, and leaving the liquid guiding groove 1240 to be exposed. Further, the first sealing member 180 may include a side wall 182 extending from an outer edge of the top wall 181. The first sealing member 180 may encase the porous ceramic liquid guiding member 124 and abut against the flange 116 and the inner surface of the first tube wall 115 for sealing, and the side wall 182 may be arranged on an outer circumference of the outer surface 124*b* of the porous ceramic liquid guiding member 124. To be specific, when the first sealing member 180 encases the porous ceramic liquid guiding member 124, the top wall 181 is arranged to contact the top face 124*a* of the porous ceramic liquid guiding member 124, and the side wall 182 may be arranged to contact the outer circumference of the outer surface 124*b* of the porous ceramic liquid guiding member 124, such that sealing may be achieved. By arranging the top wall 181 and the side wall 182 on the first sealing member 180, the sealing effect of the first sealing member 180 may be achieved, and the porous ceramic liquid guiding member 124 may be protected. Further, the first sealing member 180 may include a bottom wall 183, the bottom wall 183 may be arranged at each of two opposing sides of the first sealing member 180, and connected to an end of the side wall 181 away from the top wall 181. The bottom wall 183 may be disposed opposite to the top wall 181, and spaced apart from the top wall 181. When the first sealing member 180 encases the porous ceramic liquid guiding member 124, the bottom wall 183 may cover the stage face 124*d*. In the present embodiment, the first sealing member 180 may encase a part of the porous ceramic liquid guiding member 124 by the top wall 181, the side wall 182, and the bottom wall 183, such that firm engagement between the first sealing member 180 and the porous ceramic liquid guiding member 124 may be achieved.

Referring to FIG. 13 and FIG. 15, alternatively, the heating member 122*a* may be arranged on a bottom face 124*c* of the porous ceramic liquid guiding member 124 opposing to the liquid guiding groove 1240. The liquid in the liquid guiding groove 1240 may flow through the porous structure to the heating member 122*a*. The heating member 122*a* may be connected to the power and heated by the electric current, such that the liquid may be atomized into the smoke. In the present embodiment, the heating member 122*a* may be at least one selected from the group consisting of a heating coating, a heating circuitry, a heating plate and a heating net. For example, the heating member 122*a* may be a resistance wire. After connected to the power, the electric current may cause the heating member 122*a* to be heated, such that the liquid flowing through the porous structure to the bottom face 124*c* of the porous ceramic liquid guiding member 124 may be atomized to generate the smoke. In the present embodiment, the heating member 122*a* may be twisted and turned.

Further referring to FIG. 13 and FIG. 15, alternatively, the heating assembly 120 may further include a needle electrode 125. The needle electrode 125 may be inserted into or fixed with the bottom face 124*c* of the porous ceramic liquid guiding member 124 and extend towards a direction away from the bottom face 124*c*. The needle electrode 124 may be electrically connected to the heating member 122*a*. The needle electrode 124 may be arranged to be connected to the power, such that the electric current may flow to the heating member 122*a*. There may be two needle electrodes 125 arranged, and the two needle electrodes 125 may be connected to a positive pole and a negative pole of the power respectively. The power may be for instance a battery.

Referring to FIGS. 13 to 15, alternatively, the atomizer 301 of the present embodiment may further include a base 19 and a second sealing member 280. The base 19 may be fixedly connected to an end of the tube wall 11*a* close to the heating assembly 120. For example, at the end of the tube wall 11*a* close to the heating assembly 120, the extensive length of the second tube wall 113 along the length direction may be greater than the extensive length of the first tube wall 115 along the length direction. The base 19 may be fixedly connected to the second tube wall 113. The heating assembly 120 may be partially embedded into the space defined by the first tube wall 115 and arranged between the base 19 and the flange 16. In the present embodiment, the base 19 may be connected to the second tube wall 113 through a buckle. The base 19 may be arranged with a buckle portion 191, and an inner surface of the second tube wall 113 may define a buckle groove 1130 at a position corresponding to the buckle portion. During buckling, the buckle portion 191 may be inserted into the buckle groove 1130, such that the base 19 and the second tube wall 113 may be fixedly connected with each other through a buckled connection.

Further referring to FIGS. 13 to 15, alternatively, the second sealing member 280 may be arranged between the base 19 and the end of the tube wall 11*a* close to the heating assembly 120 for sealing, such that leakage of the smoke may be reduced. In the present embodiment, the buckle portion 191 of the base 19 may extend through the second sealing member 280 and insert into the buckle groove 1130 for fixed connection. By arranging the buckle portion 191 to extend through the second sealing member 280, a better sealing effect of the second sealing member 280 may be achieved. In the present embodiment, an atomization chamber 285 may be defined between the second sealing member 280 and the bottom face 124*c* of the porous ceramic liquid guiding member 124. The smoke generated by the heating member 122*a* may be received in the atomization chamber 285.

In the present embodiment, the air entering channel 1103 may communicate with the atomization chamber 285 and further communicate with the smoke outlet 1102, such that the external air may drive the smoke generated by the heating member 122*a* to flow to the smoke outlet 1102. The air guiding channel 10 may communicate with the liquid cavity 1101 and the atomization chamber 285, such that the air in the atomization chamber 285 may flow into the liquid cavity 1101, the pressure in the liquid cavity 1101 may be balanced with the outside, thus, obstructed flow of the liquid from the liquid cavity 1101 through the porous ceramic liquid guiding member 124 may be reduced.

Further referring to FIG. 14 and FIG. 15, the base 19 may define a mounting hole 190. In the present embodiment, the mounting hole 190 may extend through the base 19 along a height direction. A part of the second sealing member 280 may be received in the mounting hole 190 for sealing. The part of the second sealing member 280 received in the mounting hole may have a side face opposing to the heating assembly 120, and the side face may be arranged with an electrode holder 281. For example, the electrode holder 281 may be partially inserted into the second sealing member 280 for fixing. An end of the needle electrode 125 of the heating assembly 120 may be fixedly connected to the heating member 122*a*, and the other end of the needle electrode 125 may extend through the second sealing member 280, connected to the electrode holder 281, wherein the electrode holder 281 may be arranged to connect to the power. In the present embodiment, an end of the electrode holder 281 away from the heating assembly 120 may be exposed from a side of the base 19 opposing to the heating assembly 120 to form a contact, such that the power may be connected to the contact for an electric flow. Further, the atomizer 301 may include an electrode fixing element 282, arranged to encase the end of the electrode holder 281 away from the heating assembly 120, such that the electrode 281 may be fixedly positioned. The end of the electrode holder 281 away from the heating assembly 120 may be exposed from the electrode fixing element 282 to form a contact. In the present embodiment, the electrode fixing element 282 may be a plate.

In the present embodiment, the base 19 may support the porous ceramic liquid guiding member 124, such that the porous ceramic liquid guiding member 124 and the first sealing member 180 may be embedded into the liquid cavity 1101 and abut against the flange 116 for sealing. Referring to FIG. 13 and FIG. 14, for instance the base 19 may be arranged with a support pin 192 on a side facing towards the porous ceramic liquid guiding member 124. There may be two support pins 192, and the two support pins 192 may be disposed oppositely. When the base 19 is fixed with the second tube wall 113, the two support pins 192 may support the porous ceramic liquid guiding member 124. The two support pins 192 may be arranged with the second sealing member 280. The two support pins 192 may abut against two stage faces 124*d* of two sides of the porous ceramic liquid guiding member 124. That is the second sealing member 280 arranged on the support pins 192 may contact with the first sealing member 180 arranged on the stage face 124*d*.

Referring to FIG. 13 and FIG. 14, alternatively, the atomizer 301 may include a case 23, defining a space. When the case 23 is arranged under the base 19, the base 19 may be received in the space, such that the base 19 may be protected effectively.

Referring to FIGS. 13 to 15, alternatively, the atomizer 301 may include a cover assembly 24, arranged on an end of the tube wall 11*a* away from the heating assembly 120. The cover assembly 24 may at least be arranged to further guide the smoke in the smoke outlet 1102 to reach a position for a user to inhale.

In the present embodiment, the cover assembly 24 may include an outlet tube 241, a tube cover 242, and a third sealing member 243. The outlet tube 241 may be recessed inside the tube cover 242, such that the smoke outlet 1102 may communicate with the external through the outlet tube 241. Alternatively, the tube cover 242 may define a condensation chamber 2420. The outlet tube 241 allows the condensation chamber 2420 to communicate with the external, and the smoke outlet 1102 may communicate with the condensation chamber 2420. The third sealing member 243 may be arranged between the tube cover 242 and the end of the tube wall 11*a* away from the heating assembly 120 for sealing. In the present embodiment, the condensation chamber 2420 may be defined with a certain height and a certain width. To be specific, when the smoke in the smoke outlet 1102 flows with the air flow towards the outlet tube 241, some of the smoke may be condensed into a liquid in the condensation chamber 2420 and accumulate inside the condensation chamber 2420, such that the liquid generated by the condensation may not be directly inhaled into the user's mouth through the outlet tube 241. The condensation chamber 2420 is able to be defined by arranging the tube cover 242 with a certain height. That is when the tube cover 242 has a certain height, a top wall of the tube cover 242 may be spaced apart from the third sealing member 243, and the condensation chamber 2420 may be defined between the top wall of the tube cover 242 and the third sealing member 243.

Further referring to FIG. 13, alternatively, the air entering hole 100 may include a first air entering hole 101 and a second air entering hole 102. The first air entering hole 101 may be defined in the tube cover 242 and communicate with the air entering channel 1103. In the present embodiment, the first air entering hole 101 may be defined with space apart from the condensation chamber 2420. The second air entering hole 102 may be defined in the second tube wall 113 of the tube wall 11*a* and communicate with the air entering channel 1103. That is the second air entering hole 102 may extend through the second tube wall 113 corresponding to the air entering channel 1103 in order to communicate with the air entering channel 1103. The air entering channel 1103 may guide the air entering from the first and the second air entering holes 101 and 102 to the atomization chamber 285 defined between the porous ceramic liquid guiding member 124 and the base 19. According to the present embodiment, by defining the first air entering hole 101 and the second air entering hole 102 in different components, the air may enter the atomizer smoothly and efficiently. In other embodiments, there may be only one air entering hole 100 defined or a plurality of air entering holes 100 defined.

Figure 17:
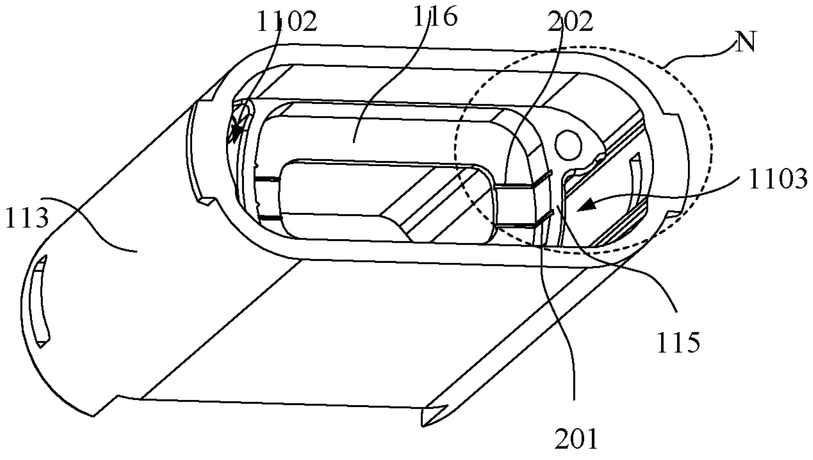
FIG. 17 is a schematic view of a smoke tube of an electronic atomization device according an embodiment of the present disclosure.
Figure 18:
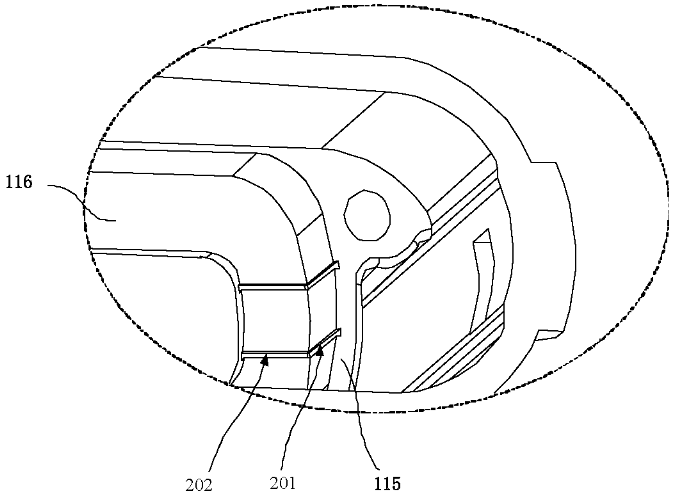
FIG. 18 is an enlarged view of an N portion of the structure shown in FIG. 17.

Referring to FIG. 17 and FIG. 18, an atomizer according to another embodiment of the present disclosure may be provided and may be substantially similar to the embodiment as described in FIGS. 12 and 13. However, in the present embodiment, the inner surface of the first tube wall 115 facing towards the heating assembly 120 may define a first air guiding recess 201. When the first sealing member 180 abuts against the inner surface of the first tube wall 115, the first air guiding recess 201 may serve as the air guiding channel 10. In the present embodiment, when the first sealing member 180 contacts the flange 116, the air guiding channel 10 may guide the air to the liquid cavity 1101, such that the negative pressure of the liquid cavity 1101 caused by atomization may be reduced, and obstructed flow of the liquid from the liquid cavity may further be reduced.

Alternatively, the surface of the flange 116 facing towards the heating assembly 120 may define a second air guiding recess 202, and the second air guiding recess 202 may communicate with the first air guiding recess 201. When the heating assembly 120 is embedded into the liquid cavity 1101 along an end of the first tube wall close to the flange 116, the first sealing member 180 may contact the inner surface of the first tube wall 115 and the flange 116, such that the first air guiding recess 201 and the second air guiding recess 202 may serve as the air guiding channel 10.

By defining the first air guiding recess 201 and the second air guiding recess 202, the air guiding channel 10 may be defined when the first sealing member 180 contacts the inner surface of the first tube wall 115 and the flange 116. The air in the atomization chamber 285 defined between the base 19 and the heating assembly 120 may be guided to the liquid cavity 1101, such that the pressure inside the liquid cavity 1101 may be balanced with the outside, and obstructed flow of the liquid may be reduced.

Alternatively, a depth of the first air guiding recess 201 may be 0.1 mm to 0.3 mm, alternatively, the depth may be 0.15 mm to 0.25 mm. The depth of the first air guiding recess may refer to a distance for which the inner surface of the first tube wall 115 recesses inwardly. A width of the first air guiding recess 201 may be 0.5 mm to 1.0 mm, alternatively, the width may be 0.7 mm to 0.8 mm. The width may refer to a width of the first air guiding recess 201 on the inner surface of the first tube wall 115. Alternatively, a depth of the second air guiding recess 202 may be 0.1 mm to 0.3 mm, alternatively, the depth may be 0.15 mm to 0.25 mm. Alternatively, a width of the second air guiding recess 202 may be 0.5 mm to 1.0 mm, alternatively, the width may be 0.7 mm to 0.8 mm.

Figure 19:
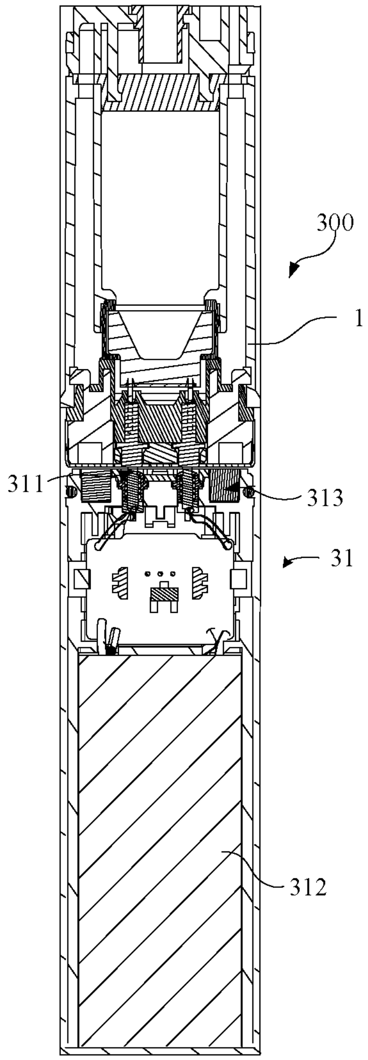
FIG. 19 is a cross sectional view of an electronic atomization device according to an embodiment of the present disclosure.

In other embodiments, the first air guiding recess 201 may be defined in the surface of the first sealing member 180 facing towards the first tube wall 115. Further, the second air guiding recess 202 may be defined on the surface of the first sealing member 180 facing towards the flange 116. In some other embodiments, the first air guiding recess 201 may be defined on the surface of the first sealing member 180 facing towards the first tube wall 115, and the second air guiding recess 202 may be defined on the surface of the flange 116 facing towards the first sealing member 180. Alternatively, the first air guiding recess 201 may be defined in the inner surface of the first tube wall 115, and the second air guiding recess 202 may be defined on the surface of the first sealing member 180 facing towards of the flange 116. When the first sealing member 180 abuts against the first tube wall 115 and the flange 116, the first air guiding recess 201 may communicate with the second air guiding recess 202. As shown in FIG. 19, the electronic atomization device 300 may be provided according to an embodiment of the present disclosure. The electronic atomization device 300 may include a power assembly 31 and an atomizer 301 as described in the above embodiments. The power assembly 31 may be configured to supply power to the atomizer 301, such that the atomizer 301 may atomize the liquid to generate the smoke.

In the present embodiment, detailed structure of the atomizer 301 may refer to the above description.

To be specific, the power assembly 31 may include at least two power contacts 311 and a cell 312. The at least two power contacts 311 may electrically connect to the cell 312, and further connected to the contacts of the electrode holder, such that power may be supplied to the atomizer 301. Further, the power assembly may include a magnetic element 313, wherein the magnetic element 313 may be arranged to fixedly connect the atomizer 301 to the power assembly 31 by magnetic attraction.

The above description is only for embodiments of the present disclosure, and does not limit the scope of the present disclosure. Any transformation with equivalent structures or equivalent processes performed by using the specification and the drawings of the present application, applied to other related fields directly or indirectly, shall be within the scope of the present disclosure.

What is claimed is:

1. An atomizer, comprising:

a lid including a liquid inlet;

a heating assembly configured to heat and atomize liquid flowing through the liquid inlet to the heating assembly;

a sealing component, arranged between the lid and the heating assembly, wherein the sealing component is configured to reduce leakage of the liquid flowing through the liquid inlet to the heating assembly, wherein the sealing component is not inserted through another sealing component; and one or more spaces formed between the sealing component and at least one of the lid and the heating assembly, wherein the one or more spaces are configured to allow external air to flow through the liquid inlet.

2. The atomizer of claim 1, wherein the atomizer further includes a shell, and wherein the shell and the lid define a liquid cavity configured to store the liquid to be vaporized, and wherein the sealing component is not inserted through the lid to the liquid cavity.

3. The atomizer of claim 1, wherein the lid includes one or more recesses, and wherein the one or more spaces are formed between the one or more recesses and the sealing component.

4. The atomizer of claim 1, wherein the sealing component includes one or more recesses, and wherein the one or more spaces are formed between the one or more recesses and the heating assembly.

5. The atomizer of claim 1, wherein the sealing component is configured to contact at least one of the lid and the heating assembly.

6. The atomizer of claim 1, wherein the atomizer further includes a base, and wherein the heating assembly is fixed between the lid and the base.

7. The atomizer of claim 6, wherein the base includes at least one air entering hole.

8. The atomizer of claim 7, wherein the base includes an air inlet board defining the at least one air entering hole, the air inlet board having a convex shape.

9. The atomizer of claim 1, wherein the lid includes a guiding portion defining a through hole extending through two opposing side surfaces of the guiding portion, and wherein the guiding portion further defines an air outlet on top of the guiding portion, such that air flows through the through hole and flows upward through the air outlet.

10. The atomizer of claim 1, wherein the heating assembly comprises a liquid guiding member, wherein the liquid guiding member defines a liquid guiding groove, and wherein the liquid guiding groove receives the liquid flowing through the liquid inlet.

11. An electronic atomization device, comprising:

an atomizer, comprising:

a lid including a liquid inlet;

a heating assembly configured to heat and atomize liquid flowing through the liquid inlet to the heating assembly;

a sealing component, arranged between the lid and the heating assembly, wherein the sealing component is configured to reduce leakage of the liquid flowing through the liquid inlet to the heating assembly, wherein the sealing component is not inserted through another sealing component; and one or more spaces formed between the sealing component and at least one of the lid and the heating assembly, wherein the one or more spaces are configured to allow external air to flow through the liquid inlet.

12. The electronic atomization device of claim 11, wherein the atomizer further includes a shell, and wherein the shell and the lid define a liquid cavity configured to store the liquid to be vaporized, and wherein the sealing component is not inserted through the lid to the liquid cavity.

13. The electronic atomization device of claim 11, wherein the lid includes one or more recesses, and wherein the one or more spaces are formed between the one or more recesses and the sealing component.

14. The electronic atomization device of claim 11, wherein the sealing component includes one or more recesses, and wherein the one or more spaces are formed between the one or more recesses and the heating assembly.

15. The electronic atomization device of claim 11, wherein the sealing component is configured to contact at least one of the lid and the heating assembly.

16. The electronic atomization device of claim 11, wherein the atomizer further includes a base, and wherein the heating assembly is fixed between the lid and the base.

17. The electronic atomization device of claim 16, wherein the base includes at least one air entering hole.

18. The electronic atomization device of claim 17, wherein the base includes an air inlet board defining the at least one air entering hole, the air inlet board having a convex shape.

19. The electronic atomization device of claim 11, wherein the lid includes a guiding portion defining a through hole extending through two opposing side surfaces of the guiding portion, and wherein the guiding portion further defines an air outlet on top of the guiding portion, such that air flows through the through hole and flows upward through the air outlet.

20. The electronic atomization device of claim 11, wherein the heating assembly comprises a liquid guiding member, wherein the liquid guiding member defines a liquid guiding groove, and wherein the liquid guiding groove receives the liquid flowing through the liquid inlet.

* * * * *